United States Patent
Iso et al.

(10) Patent No.: US 10,640,732 B2
(45) Date of Patent: May 5, 2020

(54) LENS SOLUTION, CONTACT LENS, AND PRODUCTION METHOD THEREFOR

(71) Applicants: JSR CORPORATION, Minato-ku (JP); JSR Life Sciences Corporation, Minato-ku (JP)

(72) Inventors: Kazuhiro Iso, Minato-ku (JP); Satoshi Hyugaji, Minato-ku (JP)

(73) Assignees: JSR CORPORATION, Minato-ku (JP); JSR Life Sciences Corporation, Minato-ku (JP)

( * ) Notice: Subject to any disclaimer, the term of this patent is extended or adjusted under 35 U.S.C. 154(b) by 0 days.

(21) Appl. No.: 15/116,437

(22) PCT Filed: Feb. 6, 2015

(86) PCT No.: PCT/JP2015/053423
§ 371 (c)(1),
(2) Date: Aug. 3, 2016

(87) PCT Pub. No.: WO2015/119256
PCT Pub. Date: Aug. 13, 2015

(65) Prior Publication Data
US 2017/0058237 A1   Mar. 2, 2017

(30) Foreign Application Priority Data
Feb. 6, 2014   (JP) ................................. 2014-021271

(51) Int. Cl.
| | | |
|---|---|---|
| C11D 3/37 | (2006.01) | |
| G02B 1/04 | (2006.01) | |
| G02C 7/04 | (2006.01) | |
| C11D 3/00 | (2006.01) | |
| A61F 2/16 | (2006.01) | |

(52) U.S. Cl.
CPC ............ C11D 3/0078 (2013.01); C11D 3/378 (2013.01); C11D 3/3765 (2013.01); C11D 3/3773 (2013.01); C11D 3/3784 (2013.01); G02B 1/043 (2013.01); G02C 7/049 (2013.01); A61F 2/16 (2013.01); G02C 7/04 (2013.01); G02C 2202/16 (2013.01)

(58) Field of Classification Search
CPC ....... C11D 3/37; C11D 3/3707; C11D 3/3746; G02B 1/04; G02B 1/043; G02C 7/04
See application file for complete search history.

(56) References Cited

U.S. PATENT DOCUMENTS

| | | | |
|---|---|---|---|
| 5,135,297 | A | 8/1992 | Valint, Jr. |
| 5,919,742 | A | 7/1999 | Tsuzuki et al. |
| 6,037,328 | A | 3/2000 | Hu et al. |
| 6,281,319 | B1 | 8/2001 | Mentak |
| 2004/0052746 | A1 | 3/2004 | Tamareselvy et al. |
| 2004/0241130 | A1 | 12/2004 | Tamareselvy et al. |
| 2007/0282057 | A1 | 12/2007 | Mentak et al. |
| 2010/0056647 | A1* | 3/2010 | Graham ................... A61K 8/91 514/772.5 |
| 2011/0245077 | A1* | 10/2011 | Anderson ............... A61L 15/26 502/402 |
| 2012/0114571 | A1 | 5/2012 | Klug et al. |
| 2015/0342856 | A1 | 12/2015 | Klug et al. |

FOREIGN PATENT DOCUMENTS

| | | | | |
|---|---|---|---|---|
| JP | 56-168623 | * | 5/1980 | ............... G02C 7/04 |
| JP | 10-096878 | A | 4/1998 | |
| JP | 3172179 | B2 | 6/2001 | |
| JP | 2002-542317 | A | 12/2002 | |
| JP | 2006-512425 | A | 4/2006 | |
| JP | 2007-039661 | A | 2/2007 | |
| JP | 2009-538689 | A | 11/2009 | |
| JP | 2012-501311 | A | 1/2012 | |
| JP | 2012-522852 | A | 9/2012 | |
| JP | 2013-155217 | A | 8/2013 | |

OTHER PUBLICATIONS

Japanese Office Action dated Jun. 7, 2016 for JP 2015-561064 (with English translation).
International Search Report dated Mar. 31, 2015 for PCT/JP2015/053423 filed on Feb. 6, 2015.

* cited by examiner

*Primary Examiner* — Brian P Mruk
(74) *Attorney, Agent, or Firm* — Oblon, McClelland, Maier & Neustadt, L.L.P.

(57) ABSTRACT

Provided is a lens solution which has excellent lipid detergency, exhibits high hydrophilization performance, and exhibits an excellent lipid adhesion preventive effect and an excellent lubricity-imparting effect when the solution is used to coat a lens. Disclosed is a lens solution containing a polymer having 2.5% to 95% by mass of the following repeating unit (A) and 2.5% to 95% by mass of the following repeating unit (B):

(A) a hydrophilic repeating unit; and
(B) a repeating unit having a polyoxyalkylene group in a side chain and having the end of the side chain formed from an alkyl group having 5 to 30 carbon atoms, an alkanoyl group having 5 to 30 carbon atoms, or an aryl group.

20 Claims, No Drawings

LENS SOLUTION, CONTACT LENS, AND PRODUCTION METHOD THEREFOR

TECHNICAL FIELD

The present invention relates to a lens solution, a contact lens, and a production method therefor.

BACKGROUND ART

Contact lenses are roughly classified into hydrous contact lenses (including soft contact lenses) and non-hydrous contact lenses (including hard contact lenses and soft contact lenses), and hydrous contact lenses generally have an advantage that the lenses have a more satisfactory feeling of wearing than non-hydrous contact lenses.

However, since conventional hydrous contact lenses have high hydrability, there have been problems, for example, that lenses dry up quickly, and oxygen permeability is decreased.

Thus, silicone hydrogel contact lenses, which have high oxygen permeability while being less hydratable, have been developed, and in recent years, these constitute the mainstream of contact lenses. However, silicone hydrogels have a problem that since the silicone chains contained therein exhibit hydrophobicity, the feeling of wearing is not satisfactory, and lipids easily adhere thereto. In a case where the contact lenses are continuously used in that state while leaving these problems neglected, there is a risk that, for example, eyestrain, cloudiness, lowering of the visual acuity correction power, adverse effects on the cornea, may occur.

Under such circumstances, various cleaning solutions, storage solutions and coating solutions for contact lenses have been suggested for the purpose of eliminating those lipids adhering to the lens surface, enhancing the hydrophilicity of the lens surface, preventing the adhesion of lipids, or imparting lubricity.

For example, as the cleaning solutions for contact lenses, poly(oxyethylene)-poly(oxypropylene) block copolymers (poloxamer and poloxamine), which are nonionic surfactants, have been widely used heretofore (Patent Literature 1).

CITATION LIST

Patent Literature

Patent Literature 1: U.S. Pat. No. 6,037,328 A

SUMMARY OF INVENTION

Technical Problem

However, although the aforementioned nonionic surfactants have lipid detergency, those surfactants are not satisfactory in view of the performance for hydrophilizing the contact lens surface and the performance for imparting lubricity. Furthermore, the inventors of the present invention conducted an investigation on the aforementioned nonionic surfactants, and it was found that the lipid adhesion preventive effect is also insufficient.

That is, an object of the present invention is to provide a lens solution which has excellent lipid detergency, exhibits high hydrophilization performance, and exhibits an excellent lipid adhesion preventive effect and an excellent lubricity-imparting effect when used to coat a lens.

Solution to Problem

Thus, the inventors of the present invention conducted a thorough investigation. As a result, they found that a lens solution containing a polymer which has a hydrophilic repeating unit; and a repeating unit having a polyoxyalkylene group in a side chain and having a particular hydrophobic group at the end of the side chain, respectively at particular contents, has excellent lipid detergency and also exhibits high hydrophilization performance, and when used to coat a lens, the lens solution exhibits an excellent lipid adhesion preventive effect and an excellent lubricity-imparting effect. Thus, the inventors completed the present invention.

That is, the present invention provides a lens solution containing a polymer having 2.5% to 95% by mass of the following repeating unit (A) and 2.5% to 95% by mass of the following repeating unit (B):

(A) a hydrophilic repeating unit; and
(B) a repeating unit having a polyoxyalkylene group in a side chain and having the end of the side chain formed from an alkyl group having 5 to 30 carbon atoms, an alkanoyl group having 5 to 30 carbon atoms, or an aryl group.

In addition, the present invention provides a method for producing a surface-modified contact lens, the method including bringing the solution into contact with at least a part of a contact lens surface.

Furthermore, the present invention provides a contact lens including, in at least a part of the surface, a polymer having 2.5% to 95% by mass of the following repeating unit (A) and 2.5% to 95% by mass of the following repeating unit (B):

(A) a hydrophilic repeating unit; and
(B) a repeating unit having a polyoxyalkylene group in a side chain and having the end of the side chain formed from an alkyl group having 5 to 30 carbon atoms, an alkanoyl group having 5 to 30 carbon atoms, or an aryl group.

Furthermore, it is another object of the present invention to provide a method for treating a surface of contact lens, the method including a step of bringing the solution into contact with at least a part of a contact lens surface.

Advantageous Effects of Invention

The lens solution of the present invention has excellent lipid detergency and also exhibits high hydrophilization performance, and when used to coat a lens, the lens solution exhibits an excellent lipid adhesion preventive effect and an excellent lubricity-imparting effect. Furthermore, the lens solution exhibits high adsorptiveness to lens surface and is not easily detachable.

Therefore, the lens solution of the present invention is useful as a contact lens cleaning or storage solution, and as a contact lens coating solution.

Furthermore, the contact lens of the present invention has its surface hydrophilically modified, so that lipids are unlikely adsorbed thereto, and the contact lens has excellent lubricity and excellent sustainability of those effects.

Furthermore, according to the method for producing a contact lens of the present invention, a contact lens to which lipids are unlikely to be adsorbed thereto, and which has excellent lubricity and excellent sustainability of those effects, can be produced conveniently.

DESCRIPTION OF EMBODIMENTS

Lens Solution

The lens solution of the present invention includes a polymer having 2.5% to 95% by mass of the above-described repeating unit (A) and 2.5% to 95% by mass of the above-described repeating unit (B). First, the polymer used in the present invention will be explained in detail.

(Repeating Unit (A))

A repeating unit (A) may be any hydrophilic repeating unit. The repeating unit (A) is preferably one or more selected from the group consisting of a repeating unit having a polyoxyalkylene group in a side chain and having the end of the side chain formed from a hydrogen atom or an alkyl group having 1 to 4 carbon atoms (A-1); a repeating unit represented by the following formula (3) (A-2); a repeating unit represented by the following formula (4) (A-3); a repeating unit represented by the following formula (5) (A-4); a repeating unit represented by the following formula (6) (A-5); a betaine-like repeating unit represented by the following formula (7) (A-6); an anionic repeating unit (A-7); and a cationic repeating unit represented by the following formula (8) (A-8).

Note that according to the present specification, hydrophilicity means to exhibit a property of having strong affinity to water. Specifically, in the case of a homopolymer composed only of one repeating unit (a homopolymer having a number average molecular weight of about 10,000 as measured by the measurement method of Examples), when 1 g or more of the homopolymer dissolves in 100 g of pure water at normal temperature (25° C.), the repeating unit is hydrophilic.

$$\begin{array}{c} R^6 \\ -(CH_2-C)- \\ O=C \\ O-(R^7O)_q-P-O-R^8-N^+-R^{10} \\ O^- \quad R^{11} \end{array} \tag{3}$$

in which in formula (3), $R^6$ represents a hydrogen atom or a methyl group;

$R^7$ represents an alkylene group having 2 to 4 carbon atoms;

$R^8$ represents an alkylene group having 1 to 10 carbon atoms;

$R^9$, $R^{10}$ and $R^{11}$ each independently represent a hydrogen atom or a hydrocarbon group having 1 to 8 carbon atoms; and q represents 1 to 10 as an average value.

$$\begin{array}{c} R^{12} \\ -(CH_2-C)- \\ O=C \\ N-R^{13} \\ R^{14} \end{array} \tag{4}$$

in which in formula (4), $R^{12}$ represents a hydrogen atom or a methyl group; and $R^{13}$ and $R^{14}$ each independently represent a hydrogen atom, an alkyl group having 1 to 6 carbon atoms, or a hydroxyalkyl group.

$$\begin{array}{c} R^{15} \\ -(CH_2-C)- \\ O=C \\ N-R^{16} \\ R^{17}-O \end{array} \tag{5}$$

in which in formula (5), $R^{15}$ represents a hydrogen atom or a methyl group; and $R^{16}$ and $R^{17}$ each independently represent an alkylene group having 1 to 3 carbon atoms.

$$-(CH_2-CH)- \tag{6}$$
$$\begin{array}{c} N \\ R^{18} \end{array} O$$

in which in formula (6), $R^{18}$ represents an alkylene group having 1 to 5 carbon atoms.

$$\begin{array}{c} R^{19} \\ -(CH_2-C)- \\ O=C \quad R^{22} \\ O-R^{20}-N^+-R^{21}-Y \\ R^{23} \end{array} \tag{7}$$

in which in formula (7),

Y represents —(C=O)O⁻, —(O=S=O)O⁻, —O(O=S=O)O⁻, —(S=O)O⁻, —O(S=O)O⁻, —OP(=O) (OR²⁴)O⁻, —OP(=O)(R²⁴)O⁻, —P(=O) (OR²⁴)O⁻, or —P(=O) (R²⁴)O⁻ (in which $R^{24}$ represents an alkyl group having 1 to 3 carbon atoms);

$R^{19}$ represents a hydrogen atom or a methyl group;

$R^{20}$ and $R^{21}$ each independently represent a divalent organic group having 1 to 10 carbon atoms; and $R^{22}$ and $R^{23}$ each independently represent a hydrocarbon group having 1 to 10 carbon atoms.

$$\begin{array}{c} R^{25} \\ -(CH_2-C)- \\ R^{28} \\ R^{26}-R^{27}-N^+-R^{30} \\ R^{29} \end{array} \tag{8}$$

in which in formula (8), $R^{25}$ represents a hydrogen atom or a methyl group;

$R^{26}$ represents —O—, *—(C=O)—O—, *—(C=O)—NR³¹—, *—NR³¹—(C=O)— (in which $R^{31}$ represents a hydrogen atom or an organic group having 1 to 10 carbon atoms; and the symbol * represents the position at which the moiety is bonded to the carbon atom to which $R^{25}$ in formula (8) is bonded), or a phenylene group;

$R^{27}$ represents a divalent organic group having 1 to 10 carbon atoms; and $R^{28}$, $R^{29}$ and $R^{30}$ each independently represent a hydrocarbon group having 1 to 10 carbon atoms.

(Repeating Unit (A-1))

The repeating unit (A-1) has a polyoxyalkylene group in a side chain, and has the end of the side chain formed from a hydrogen atom or an alkyl group having 1 to 4 carbon atoms.

An example of the repeating unit (A-1) is a repeating unit containing a structure represented by the following formula (1) in a side chain. Regarding a polymer species that constitutes a repeating unit having the structure represented by formula (1) in a side chain, any known polymer can be used, and above all, for example, a (meth)acrylate-based polymer species, a (meth)acrylamide-based polymer species, or a styrene-based polymer species is preferred. Among these, a repeating unit represented by the following formula (2) is preferred.

(1)

in which in formula (1), $R^1$ represents an alkylene group having 2 to 4 carbon atoms;

$R^2$ represents a hydrogen atom or an alkyl group having 1 to 4 carbon atoms; and n represents 2 to 100 as an average value.

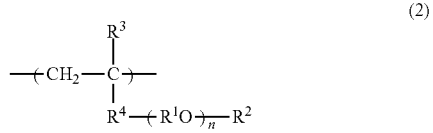
(2)

in which in formula (2), $R^3$ represents a hydrogen atom or a methyl group;

$R^4$ represents —O—, *—(C=O)—O—, *—(C=O)—NR$^5$—, *—NR$^5$—(C=O)— (in which $R^5$ represents a hydrogen atom or an organic group having 1 to 10 carbon atoms; and the symbol * represents the position at which the moiety is bonded to the carbon atom to which $R^3$ in formula (2) is bonded), or a phenylene group; and other variables have the same meanings as those of formula (1), respectively.

Here, the respective variables in formulae (1) and (2) will be explained.

$R^1$ represents an alkylene group having 2 to 4 carbon atoms, and n $R^1$s may be identical or different.

The number of carbon atoms of the alkylene group represented by $R^1$ is preferably 2 or 3, and more preferably 2.

Furthermore, the alkylene group represented by $R^1$ may be linear or branched, and specific examples thereof include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group. Among these, from the viewpoints of, for example, easy availability and impartation of hydrophilicity, an ethane-1,2-diyl group is preferred.

Furthermore, $R^2$ represents a hydrogen atom or an alkyl group having 1 to 4 carbon atoms. The number of carbon atoms of the alkyl group represented by $R^2$ is preferably 1 to 3, more preferably 1 or 2, and even more preferably 1, from the viewpoints of, for example, easy availability and impartation of hydrophilicity. Furthermore, the alkyl group represented by $R^2$ may be linear or branched, and specific examples thereof include a methyl group, an ethyl group, an n-propyl group, an isopropyl group, an n-butyl group, an isobutyl group, a sec-butyl group, and a tert-butyl group.

Among the groups for $R^2$ as such, from the viewpoints of, for example, easy availability and impartation of hydrophilicity, a hydrogen atom or an alkyl group having 1 to 3 carbon atoms is preferred; a hydrogen atom or an alkyl group having 1 or 2 carbon atoms is more preferred; a hydrogen atom or a methyl group is even more preferred; and a methyl group is particularly preferred.

$R^4$ represents —O—, *—(C=O)—O—, *—(C=O)—NR$^5$—, *—NR$^5$—(C=O)—, or a phenylene group. Examples of such a phenylene group include a 1,2-phenylene group, a 1,3-phenylene group, and a 1,4-phenylene group.

Furthermore, the number of carbon atoms of the organic group represented by $R^5$ is 1 to 10, and is preferably 1 to 6. The aforementioned organic group may be a hydrocarbon group. Such a hydrocarbon group is a concept including an aliphatic hydrocarbon group, an alicyclic hydrocarbon group, and an aromatic hydrocarbon group.

The aliphatic hydrocarbon group for $R^5$ may be linear or branched, and specific examples thereof include an alkyl group such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, and a decyl group.

Furthermore, the alicyclic hydrocarbon group is roughly classified into a monocyclic alicyclic hydrocarbon group and a bridged cyclic hydrocarbon group. Examples of the monocyclic alicyclic hydrocarbon group include a cycloalkyl group such as a cyclopropyl group and a cyclohexyl group. Furthermore, examples of the bridged cyclic hydrocarbon group include an isobornyl group.

Furthermore, examples of the aromatic hydrocarbon group include an aryl group such as a phenyl group.

Among the groups for $R^4$ such as described above, from the viewpoint of, for example, impartation of hydrophilicity, *—(C=O)—O— or a phenylene group is preferred, and *—(C=O)—O— is particularly preferred.

n represents 2 to 100 as an average value, and is preferably 4 to 90 as an average value, more preferably 8 to 90 as an average value, even more preferably 8 to 60 as an average value, still more preferably 8 to 40 as an average value, and particularly preferably 9 to 25 as an average value. Meanwhile, the various "average values" in the present specification can be analyzed by NMR. For example, the average value of n can be calculated by analyzing the structure of the formula (2) described above by $^1$H-NMR, and comparing the integrated values of the respective proton peaks of the alkylene group having 2 to 4 carbon atoms for $R^1$ and the terminal methyl group of the alkyl group having 1 to 4 carbon atoms for $R^2$.

Examples of the monomer from which such a repeating unit (A-1) is derived include polyethylene glycol (meth)acrylate, polypropylene glycol (meth)acrylate, polyethylene glycol polypropylene glycol (meth)acrylate, polyethylene glycol polytetramethylene glycol (meth)acrylate, polypropylene glycol polytetramethylene glycol (meth)acrylate, methoxypolyethylene glycol (meth)acrylate, and ethoxypolyethylene glycol (meth)acrylate. The repeating unit (A-1) may be used singly or as a combination of two or more thereof. Among these, polyethylene glycol (meth)acrylate or methoxypolyethylene glycol (meth)acrylate is preferred.

(Repeating Unit (A-2))

The repeating unit (A-2) is represented by the formula (3) described above.

In formula (3), $R^7$ represents an alkylene group having 2 to 4 carbon atoms. Note that when there are plural $R^7$s, each of $R^7$ may be identical or different.

Furthermore, the number of carbon atoms of the alkylene group represented by $R^7$ is preferably 2 or 3, and more preferably 2.

The alkylene group represented by $R^7$ may be linear or branched, and specific examples thereof include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group. Among these, from the viewpoints of, for example, easy availability and impartation of hydrophilicity, an ethane-1,2-diyl group is preferred.

Furthermore, $R^8$ represents an alkylene group having 1 to 10 carbon atoms.

The number of carbon atoms of the alkylene group represented by $R^8$ is preferably 1 to 6, more preferably 1 to 4, even more preferably 2 or 3, and particularly preferably 2.

Furthermore, the alkylene group represented by $R^8$ may be linear or branched, and specific suitable examples thereof include the same groups as the alkylene groups represented by $R^7$.

Furthermore, $R^9$, $R^{10}$ and $R^{11}$ each independently represent a hydrogen atom or a hydrocarbon group having 1 to 8 carbon atoms; and a hydrocarbon group having 1 to 8 carbon atoms is preferred. The number of carbon atoms of such a hydrocarbon group is preferably 1 to 4, more preferably 1 or 2, and particularly preferably 1.

Examples of the hydrocarbon group include an alkyl group, an aryl group such as a phenyl group; and an aralkyl group such as a benzyl group. An alkyl group is preferred.

The alkyl group may be linear or branched, and specific suitable examples thereof include a methyl group, an ethyl group, an n-propyl group, an isopropyl group, an n-butyl group, an isobutyl group, a sec-butyl group, and a tert-butyl group.

Furthermore, q represents 1 to 10 as an average value, and is preferably 1 to 7 as an average value, more preferably 1 to 4 as an average value, and even more preferably 1.

Examples of the monomer from which such a repeating unit (A-2) is derived include 2-(meth)acryloyloxyethyl-2'-(trimethylammonio)ethyl phosphate (2-(meth)acryloyloxyethyl phosphorylcholine), 3-(meth)acryloyloxypropyl-2'-(trimethylammonio)ethyl phosphate, 4-(meth)acryloyloxybutyl-2'-(trimethylammonio)ethyl phosphate, 2-(meth)acryloyloxyethoxyethyl-2'-(trimethylammonio)ethyl phosphate, 2-(meth)acryloyloxydiethoxyethyl-2'-(trimethylammonio)ethyl phosphate, 2-(meth)acryloyloxyethyl-2'-(triethylammonio)ethyl phosphate, and 2-(meth)acryloyloxyethyl-2'-(tributylammonio)ethyl phosphate. The repeating unit (A-2) may be used singly or in combination of two or more thereof.

(Repeating Unit (A-3))

The repeating unit (A-3) is represented by the formula (4) described above.

In formula (4), $R^{13}$ and $R^{14}$ each independently represent a hydrogen atom, an alkyl group having 1 to 6 carbon atoms, or a hydroxyalkyl group.

The number of carbon atoms of the alkyl group represented by $R^{13}$ and $R^{14}$ is preferably 1 to 3.

Furthermore, the alkyl group represented by $R^{13}$ or $R^{14}$ may be linear or branched, and specific suitable examples thereof include a methyl group, an ethyl group, an n-propyl group, and an isopropyl group.

Furthermore, the number of carbon atoms of the hydroxyalkyl group represented by $R^{13}$ and $R^{14}$ is preferably 1 to 6, and more preferably 1 to 3. The alkyl group contained in the hydroxyalkyl group may be linear or branched, and specific suitable examples of the hydroxyalkyl group include a hydroxymethyl group, a hydroxyethyl group, a hydroxypropyl group, and a hydroxyisopropyl group. Note that the position of substitution of the hydroxyl group in the hydroxyalkyl group is arbitrary.

Examples of the monomer from which such a repeating unit (A-3) is derived include dimethyl (meth)acrylamide, diethyl (meth)acrylamide, N-isopropyl (meth)acrylamide, N-(hydroxymethyl) (meth)acrylamide, and N-(2-hydroxyethyl) (meth)acrylamide. The repeating unit (A-3) may be used singly or in combination of two or more thereof.

(Repeating Unit (A-4))

The repeating unit (A-4) is represented by the formula (5) described above.

In formula (5), $R^{16}$ and $R^{17}$ each independently represent an alkylene group having 1 to 3 carbon atoms. The number of carbon atoms of such an alkylene group is preferably 1 or 2.

Furthermore, the alkylene group may be linear or branched; and the alkylene group is preferably linear. Specific suitable examples thereof include a methane-1,1-diyl group and an ethane-1,2-diyl group.

Examples of the monomer from which such a repeating unit (A-4) is derived include 4-(meth)acryloylmorpholine.

(Repeating Unit (A-5))

The repeating unit (A-5) is represented by the formula (6) described above.

In formula (6), $R^{18}$ represents an alkylene group having 1 to 5 carbon atoms. The number of carbon atoms of such an alkylene group is preferably 3 to 5.

Furthermore, the alkylene group may be linear or branched; and the alkylene group is preferably linear. Specific suitable examples thereof include a propane-1,3-diyl group, a butane-1,4-diyl group, and a pentane-1,5-diyl group.

Examples of the monomer from which such a repeating unit (A-5) is derived include 1-vinyl-2-pyrrolidone and N-vinyl-ε-caprolactam, and the repeating unit (A-5) may used singly or in combination of two or more thereof.

(Repeating Unit (A-6))

The repeating unit (A-6) is a betaine-like repeating unit represented by the formula (7) described above.

In formula (7), Y is preferably —(C=O)O. Note that examples of the alkyl group represented by $R^{24}$ include a methyl group, an ethyl group, an n-propyl group, and an isopropyl group.

Furthermore, in formula (7), $R^{20}$ and $R^{21}$ each independently represent a divalent organic group having 1 to 10 carbon atoms. The number of carbon atoms of such a divalent organic group is preferably 1 to 8, and more preferably 1 to 6.

Furthermore, the divalent organic group is preferably a divalent hydrocarbon group, and more preferably a divalent aliphatic hydrocarbon group. The divalent aliphatic hydrocarbon group may be linear or branched. Also, the divalent aliphatic hydrocarbon group is preferably an alkylene group. Examples of the divalent aliphatic hydrocarbon group include a methane-1,1-diyl group, an ethane-1,2-diyl group, a propane-1,1-diyl group, a propane-1,2-diyl group, a propane-1,3-diyl group, a propane-2,2-diyl group, a butane-1,4-diyl group, a pentane-1,5-diyl group, and a hexane-1,6-diyl group.

Furthermore, in formula (7), $R^{22}$ and $R^{23}$ each independently represent a hydrocarbon group having 1 to 10 carbon atoms. The number of carbon atoms of the hydrocarbon group is preferably 1 to 6, and more preferably 1 to 4.

Examples of the hydrocarbon group represented by $R^{22}$ and $R^{23}$ include an alkyl group; an aryl group such as a phenyl group; and an aralkyl group such as a benzyl group; and an alkyl group is preferred. The alkyl group may be linear or branched, and examples thereof include a methyl group, an ethyl group, an n-propyl group, an isopropyl group, an n-butyl group, an isobutyl group, a sec-butyl group, and a tert-butyl group.

Examples of the monomer from which such a repeating unit (A-6) is derived include a (meth)acrylate-based monomer such as N-(meth)acryloyloxyethyl-N,N-dimethylammonium-α-N-methylcarboxybetaine and N-(meth)acryloyloxyethyl-N,N-dimethylammonium-α-N-propylsulfobetaine. The repeating unit (A-6) may be used singly or in combination of two or more thereof.

(Repeating Unit (A-7))

The repeating unit (A-7) is an anionic repeating unit.

Examples of the repeating unit (A-7) include a repeating unit having an acidic group.

Furthermore, regarding the repeating unit (A-7), from the viewpoint of easy availability and safety, a unit derived from a monomer containing an ethylenically unsaturated bond is preferred.

Examples of the acidic group include a carboxyl group, a sulfo group, a phosphoric acid group, or a salt thereof, and a repeating unit may have one of these acidic groups, or may have two or more thereof. Note that examples of the salts include alkali metal salts such as a sodium salt and a potassium salt; alkaline earth metal salts such as a magnesium salt and a calcium salt; an ammonium salt; and an organic ammonium salt.

Examples of the monomer from which the repeating unit (A-7) is derived include an unsaturated dicarboxylic acid such as fumaric acid, maleic acid and itaconic acid, or a salt thereof; an unsaturated carboxylic acid such as (meth)acrylic acid, or a salt thereof; a sulfo group-containing polymerizable unsaturated monomer such as ethylenesulfonic acid, allylsulfonic acid, methallyl sulfonic acid, 2-sulfoethyl (meth)acrylate, and 2-acrylamido-2-methylpropanesulfonic acid, or a salt thereof; and a phosphoric acid group-containing polymerizable unsaturated monomer such as 2-(meth)acryloyloxyethyl acid phosphate and 2-(meth)acryloyloxypropyl acid phosphate, or a salt thereof. Furthermore, the monomer from which the repeating unit (A-7) is derived may also be obtained using, for example, a hydrolysate of an acrylic acid ester; a hydrolysate of an acid anhydride of an unsaturated dicarboxylic acid such as maleic anhydride or itaconic anhydride; or an adduct of an acidic group-containing thiol to an epoxy group of glycidyl methacrylate or (4-vinylbenzyl) glycidyl ether or the like. The repeating unit (A-7) may be used singly or in combination of two or more thereof.

Among these, from the viewpoints of easy availability and reactivity, acrylic acid, or methacrylic acid is preferred.

(Repeating Unit (A-8))

The repeating unit (A-8) is a cationic repeating unit represented by the formula (8) described above.

In formula (8), $R^{26}$ represents —O—, *—(C=O)—O—, *—(C=O)—NR$^{31}$—, *—NR$^{31}$—(C=O)—, or a phenylene group. Examples of such a phenylene group include a 1,2-phenylene group, a 1,3-phenylene group, and a 1,4-phenylene group.

The number of carbon atoms of the organic group represented by $R^{31}$ is 1 to 10, and is preferably 1 to 6. Examples of the organic group include a hydrocarbon group. Such a hydrocarbon group is a concept including an aliphatic hydrocarbon group, an alicyclic hydrocarbon group, and an aromatic hydrocarbon group.

The aliphatic hydrocarbon group for $R^{31}$ may be linear or branched, and specific examples thereof include an alkyl group such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, and a decyl group.

Furthermore, the alicyclic hydrocarbon group is roughly classified into a monocyclic alicyclic hydrocarbon group and a bridged cyclic hydrocarbon group. Examples of the monocyclic alicyclic hydrocarbon group include a cycloalkyl group such as a cyclopropyl group and a cyclohexyl group. Furthermore, examples of the bridged cyclic hydrocarbon group include an isobornyl group.

Furthermore, examples of the aromatic hydrocarbon group include an aryl group such as a phenyl group.

In formula (8), $R^{27}$ represents a divalent organic group having 1 to 10 carbon atoms. The number of carbon atoms of such a divalent organic group is preferably 1 to 8, and more preferably 1 to 6.

Furthermore, regarding the divalent organic group, a divalent hydrocarbon group is preferred, and a divalent aliphatic hydrocarbon group is more preferred. The divalent aliphatic hydrocarbon group may be linear or branched. The divalent aliphatic hydrocarbon group is preferably an alkylene group. Examples thereof include a methane-1,1-diyl group, an ethane-1,2-diyl group, a propane-1,1-diyl group, a propane-1,2-diyl group, a propane-1,3-diyl group, a propane-2,2-diyl group, a butane-1,4-diyl group, a pentane-1,5-diyl group, and a hexane-1,6-diyl group.

In formula (8), $R^{28}$, $R^{29}$ and $R^{30}$ independently represent a hydrocarbon group having 1 to 10 carbon atoms. The number of carbon atoms of the hydrocarbon group is preferably 1 to 6, and more preferably 1 to 4.

Examples of the hydrocarbon group represented by $R^{28}$, $R^{29}$ and $R^{30}$ include an alkyl group; an aryl group such as a phenyl group; and an aralkyl group such as benzyl group; and an alkyl group is preferred. The alkyl group may be linear or branched, and examples thereof include a methyl group, an ethyl group, an n-propyl group, an isopropyl group, an n-butyl group, an isobutyl group, a sec-butyl group, and a tert-butyl group.

Note that the repeating unit (A-8) may have a counterion. Examples of the counterion include a halogeno ion such as chlorine ion, bromine ion, and iodine ion; a hydrogen sulfide ion; an alkylsulfuric acid ion such as methylsulfuric acid ion and ethylsulfuric acid ion; an alkylsulfonic acid ion; an arylsulfonic acid ion such as dodecylbenzenesulfonic acid ion and para-toluenesulfonic acid ion; an alkenylsulfonic acid ion such as sodium 2-methyl-2-propene-1-sulfonate; and a carboxylic acid ion such as acetic acid ion.

Specific suitable examples of the monomer species of the monomer from which the repeating unit (A-8) is derived, include a (meth)acrylate and a (meth)acrylamide.

Examples of the monomer species of (meth)acrylate include a ((meth)acryloyloxy-$C_{1-10}$ alkyl)-tri-$C_{1-10}$ alkylammonium chloride such as ((meth)acryloyloxyethyl)trimethylammonium chloride; and a ((meth)acryloyloxy-$C_{1-10}$ alkyl)-di-$C_{1-10}$ alkyl-$C_{6-10}$ aralkylammonium chloride such as ((meth)acryloyloxyethyl)dimethylbenzylammonium chloride. Examples of the monomer species of (meth)acrylamide include (3-(meth)acrylamido-$C_{1-10}$ alkyl)-tri-$C_{1-10}$ alkylammonium chloride such as (3-(meth)acrylamidopropyl)trimethylammonium chloride; and (3-(meth)acrylamido-$C_{1-10}$ alkyl)-di-$C_{1-10}$ alkyl-$C_{6-10}$ aralkylammonium chloride such as (3-(meth)acrylamidopropyl)dimethylbenzylammonium chloride. The repeating unit (A-8) may be used singly or in combination of two or more thereof.

Among these, from the viewpoints of easy availability and reactivity, (3-(meth)acrylamidopropyl)trimethylammonium chloride is preferred.

Among these repeating units (A-1) to (A-8), from the viewpoints of lipid detergency, hydrophilization performance, peeling resistance, a lipid adhesion preventive effect, and a lubricity-imparting effect, the repeating unit (A-1), repeating unit (A-3), repeating unit (A-4), repeating unit (A-6), and repeating unit (A-7) are preferred, and the repeating unit (A-1), repeating unit (A-3), repeating unit (A-6) and repeating unit (A-7) are more preferred.

Also, in a case where these repeating units are used in combination, regarding the combination, from the viewpoints of hydrophilization performance, peeling resistance, and a lubricity-imparting effect, a combination of one or more selected from the group consisting of the repeating units (A-1) and (A-3), and one or more selected from the group consisting of the repeating units (A-6) and (A-7) is preferred, and a combination of the repeating unit (A-3) and one or more selected from the group consisting of the repeating units (A-6) and (A-7) is more preferred, and a combination of the repeating unit (A-3) and the repeating unit (A-6) is particularly preferred.

Furthermore, a total content of the repeating unit (A) is 2.5% to 95% by mass in the polymer; and from the viewpoints of lipid detergency, hydrophilization performance, peeling resistance, a lipid adhesion preventive effect and a lubricity-imparting effect, and from the viewpoint of enhancing the water-solubility of the polymer, the total content is preferably 5% to 95% by mass, more preferably 20% to 95% by mass, even more preferably 30% to 95% by mass, and still more preferably 40% to 90% by mass.

Furthermore, in a case where the lens solution of the present invention is intended for contact lens cleaning or for storage, the total content is particularly preferably 50% to 90% by mass from the viewpoints of lipid detergency and impartation of hydrophilicity. On the other hand, in a case where the lens solution of the present invention is used as a contact lens coating agent, from the viewpoints of impartation of hydrophilicity, peeling resistance and a lubricity impartation effect, the total content is more preferably 30% to 95% by mass, and particularly preferably 40% to 90% by mass.

Furthermore, in a case where one or more selected from the group consisting of the repeating units (A-1) and (A-3) and one or more selected from the group consisting of the repeating units (A-6) and (A-7) are used in combination, the content ratio thereof is, in terms of a mass ratio, preferably 60:40 to 99.9:0.1, more preferably 75:25 to 99:1, even more preferably 80:20 to 99:1, and particularly preferably 85:15 to 99:1.

Note that the content of the repeating unit (A) can be analyzed by, for example, $^1$H-NMR or $^{13}$C-NMR.

(Repeating Unit (B))

The repeating unit (B) is a repeating unit having a polyoxyalkylene group in a side chain, and has the end of the side chain formed from an alkyl group having 5 to 30 carbon atoms, an alkanoyl group having 5 to 30 carbon atoms, or an aryl group. A polymer may have one or two or more of repeating units corresponding to the repeating unit (B).

An example of such a repeating unit (B) is a repeating unit containing a structure represented by the following formula (9) in a side chain. Regarding a polymer species that constitutes a repeating unit having a structure represented by formula (9) in a side chain, any known polymer species can be used, and above all, for example, a (meth)acrylate-based polymer species, a (meth)acrylamide-based polymer species, or a styrene-based polymer species is preferred. Among them, a repeating unit represented by the following formula (10) is preferred.

(9)

in which in formula (9), $R^{32}$ represents an alkylene group having 2 to 4 carbon atoms;

$R^{33}$ represents an alkyl group having 5 to 30 carbon atoms, an alkanoyl group having 5 to 30 carbon atoms, or an aryl group; and m represents 2 to 100 as an average value.

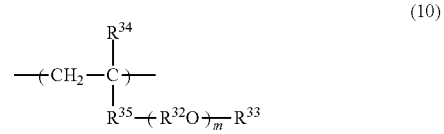

(10)

in which in formula (10), $R^{34}$ represents a hydrogen atom or a methyl group;

$R^{35}$ represents —O—, —(C=O)—O—, —(C=O)—NR$^{36}$, —NR$^{36}$—(C=O)— (in which $R^{36}$ represents a hydrogen atom or an organic group having 1 to 10 carbon atoms; and the symbol  represents the position at which the moiety is bonded to the carbon atom to which $R^{34}$ in formula (10) is bonded), or a phenylene group; and other variables have the same meanings as those of formula (9).

Here, the various symbols in formulae (9) and (10) will be explained.

$R^{32}$ represents an alkylene group having 2 to 4 carbon atoms. The number of carbon atoms of the alkylene group represented by $R^{32}$ is preferably 2 or 3, and more preferably 2.

Furthermore, the alkylene group represented by $R^{32}$ may be linear or branched, and specific examples thereof include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group. Among these, from the viewpoints of, for example, easy availability and lipid detergency, an ethane-1,2-diyl group is preferred.

Note that m $R^{32}$s may be identical or different.

Furthermore, $R^{33}$ represents an alkyl group having 5 to 30 carbon atoms, an alkanoyl group having 5 to 30 carbon atoms, or an aryl group.

The number of carbon atoms of the alkyl group or alkanoyl group represented by $R^{33}$ is preferably 6 to 25, more preferably 7 to 20, even more preferably 8 to 18, still more preferably 9 to 16, and particularly preferably 10 to 14, from the viewpoints of, for example, easy availability and lipid detergency.

Furthermore, the alkyl group represented by $R^{33}$ may be linear or branched, and specific examples thereof include a 2-ethylhexyl group, an octyl group, a decyl group, a lauryl group, a palmityl group, and a stearyl group. Among these, a 2-ethylhexyl group, a lauryl group or a stearyl group is preferred, and a lauryl group or a stearyl group is more preferred.

Furthermore, examples of the alkanoyl group represented by $R^{33}$ include a 2-ethylhexanoyl group, a lauroyl group, and a stearoyl group.

The number of carbon atoms of the aryl group represented by $R^{33}$ is 6 to 12. A specific example thereof is a phenyl group.

Furthermore, the aryl group may have an alkyl group having 1 to 30 carbon atoms as a substituent. The number of carbon atoms of such an alkyl group is preferably 3 to 24, and more preferably 5 to 16. Note that the position of substitution and the number of substitutions of such a substituted alkyl group are arbitrary; and a suitable number of substitutions is 1 or 2.

Furthermore, examples of an aryl group having such an alkyl group having 1 to 30 carbon atoms as a substituent include a nonylphenyl group.

Among the groups for $R^{33}$ as described above, from the viewpoints of, for example, easy availability and lipid detergency, an alkyl group having 5 to 30 carbon atoms or an aryl group is preferred, and an alkyl group having 5 to 30 carbon atoms is more preferred.

Furthermore, $R^{35}$ represents —O—, —(C=O)—O—, —(C=O)—NR$^{36}$—, **—NR$^{36}$—(C=O)—, or a phenylene group. Examples of such a phenylene group include a 1,2-phenylene group, a 1,3-phenylene group, and a 1,4-phenylene group.

The number of carbon atoms of the organic group represented by $R^{36}$ is 1 to 10, and is preferably 1 to 6. Examples of the organic group include a hydrocarbon group. Such a hydrocarbon group is a concept including an aliphatic hydrocarbon group, an alicyclic hydrocarbon group, and an aromatic hydrocarbon group.

The aliphatic hydrocarbon group for $R^3$ may be linear or branched, and specific examples thereof include alkyl groups such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, and a decyl group.

Furthermore, the alicyclic hydrocarbon group is roughly classified into a monocyclic alicyclic hydrocarbon group and a bridged cyclic hydrocarbon group. Examples of the monocyclic alicyclic hydrocarbon group include cycloalkyl groups such as a cyclopropyl group and a cyclohexyl group. Also, examples of the bridged cyclic hydrocarbon group include an isobornyl group.

Examples of the aromatic hydrocarbon group include an aryl group such as a phenyl group.

Among the groups for $R^{35}$ as described above, —(C=O)—O— or a phenylene group is preferred, and —(C=O)—O— is particularly preferred.

m represents 2 to 100 as an average value, and is preferably 2 to 90 as an average value, more preferably 4 to 90 as an average value, even more preferably 9 to 60 as an average value, and particularly preferably 10 to 40 as an average value.

Examples of the monomer from which such a repeating unit (B) is derived include 2-ethylhexyl polyethylene glycol (meth)acrylate, lauroxypolyethylene glycol (meth)acrylate, stearoxypolyethylene glycol (meth)acrylate, phenoxypolyethylene glycol (meth)acrylate, phenoxypolypropylene glycol (meth)acrylate, nonylphenoxypolypropylene glycol (meth)acrylate, 2-ethylhexyl polyethylene glycol polypropylene glycol (meth)acrylate, and nonylphenoxypolyethylene glycol polypropylene glycol (meth)acrylate. The repeating unit (B) may be used singly or in combination of two or more thereof. Among these, lauroxypolyethylene glycol (meth)acrylate or stearoxypolyethylene glycol (meth)acrylate is preferred.

A total content of the repeating unit (B) is 2.5% to 95% by mass in the polymer; and from the viewpoints of lipid detergency, hydrophilization performance, peeling resistance, and a lipid adhesion preventive effect, and from the viewpoint of enhancing the water-solubility of the polymer, the total content is preferably 5% to 95% by mass, more preferably 5 to 80% by mass, even more preferably 10 to 70% by mass, and still more preferably 10% to 60% by mass.

Furthermore, in a case where the lens solution of the present invention is intended for contact lens cleaning or for storage, from the viewpoints of lipid detergency and impartation of hydrophilicity, the total content is particularly preferably 10% to 50% by mass. On the other hand, in a case where the lens solution of the present invention is used as a contact lens coating agent, from the viewpoints of impartation of hydrophilicity and peeling resistance, the total content is particularly preferably 10% to 60% by mass.

Note that the content of the repeating unit (B) may be analyzed in the same manner as in the case of the content of the repeating unit (A).

(Repeating Unit (C))

It is preferable that the polymer used in the present invention has one or more repeating unit (C) selected from the group consisting of a repeating unit (C-1) represented by the following formula (11) and a repeating unit (C-2) having a group represented by the following formula (12) at the end of a side chain. When the polymer includes such repeating units (C), the hydrophilization performance is enhanced, and the polymer is unlikely peeled off from the lens surface.

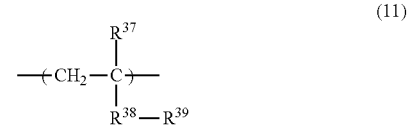

(11)

in which in formula (11), $R^{37}$ represent a hydrogen atom or a methyl group;

$R^{38}$ represents —O—, *—(C=O)—O—, *—(C=O)—NR$^{40}$—, *—NR$^4$—(C=O)— (in which $R^{40}$ represents a hydrogen atom or an organic group having 1 to 10 carbon atoms; and the symbol * represents the position at which the moiety is bonded to the carbon atom to which $R^{37}$ in formula (11) is bonded), or a phenylene group; and $R^{39}$ represents a hydrocarbon group having 4 to 30 carbon atoms.

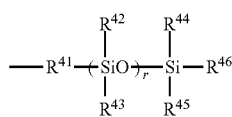

(12)

in which in formula (12), $R^{41}$ represents a divalent organic group having 1 to 10 carbon atoms;

$R^{42}$ and $R^{43}$ each independently represent an organic group having 1 to 10 carbon atoms;

$R^{44}$, $R^{45}$ and $R^{46}$ independently represent —OSi$(R^{49})_3$ (in which $R^{49}$ independently represent a hydrogen atom or an organic group having 1 to 8 carbon atoms), or an organic group having 1 to 10 carbon atoms; and r represents 0 to 200 as an average value.

(Repeating Unit (C-1))

The repeating unit (C-1) is represented by the formula (11) described above.

$R^{38}$ represents —O—, *—(C=O)—O—, *—(C=O)—NR$^{40}$, ***—NR$^{40}$—(C=O)—, or a phenylene group. Examples of such a phenylene group include a 1,2-phenylene group, a 1,3-phenylene group, and a 1,4-phenylene group.

The number of carbon atoms of the organic group represented by $R^{40}$ is 1 to 10, and is preferably 1 to 6. Examples of the aforementioned organic group include a hydrocarbon group. Such a hydrocarbon group is a concept including an aliphatic hydrocarbon group, an alicyclic hydrocarbon group, and an aromatic hydrocarbon group.

The aliphatic hydrocarbon group for $R^{40}$ may be linear or branched, and specific examples thereof include an alkyl group such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, and a decyl group.

Furthermore, the alicyclic hydrocarbon group is roughly classified into a monocyclic alicyclic hydrocarbon group and a bridged cyclic hydrocarbon group. Examples of the monocyclic alicyclic hydrocarbon group include a cycloalkyl group such as a cyclopropyl group and a cyclohexyl group. Furthermore, examples of the bridged cyclic hydrocarbon group include an isobornyl group.

Furthermore, examples of the aromatic hydrocarbon group include an aryl group such as a phenyl group.

Among the groups for $R^{38}$ as described above, from the viewpoint of enhancing lipid detergency and hydrophilization performance, as well as from the viewpoint of unlikely making the polymer peeling from the lens surface, *—(C=O)—O—, *—(C=O)—NR$^{40}$—, or a phenylene group is preferred, *—(C=O)—O— or *—(C=O)—NR$^{40}$— is more preferred, and *—(C=O)—O— or *—(C=O)—NH— is particularly preferred.

Furthermore, $R^{39}$ represents a hydrocarbon group having 4 to 30 carbon atoms, and may be linear or branched, or may contain a cyclic structure. $R^{39}$ is preferably an alkyl group.

Furthermore, the number of carbon atoms of the hydrocarbon group is preferably 6 to 24, more preferably 8 to 18, and even more preferably 8 to 14.

Examples of the alkyl group include a 2-ethylhexyl group, an octyl group, a decyl group, a lauryl group, a palmityl group, and a stearyl group. Among these, from the viewpoints of, for example, easy availability and lipid detergency, a 2-ethylhexyl group, a lauryl group and a stearyl group are preferred, and a 2-ethylhexyl group and a lauryl group are more preferred.

Examples of the monomer from which such a repeating unit (C-1) is derived include 2-ethylhexyl (meth)acrylate, lauryl (meth)acrylate, and stearyl (meth)acrylate. The repeating unit (C-1) may be used singly or in combination of two or more thereof.

(Repeating Unit (C-2))

Regarding a polymer species that constitutes a repeating unit having a group represented by the formula (12) described above at the end of a side chain, any known polymer species can be used, and above all, for example, a (meth)acrylate-based polymer species, a (meth)acrylamide-based polymer species, or a styrene-based polymer species is preferred. Among these, a repeating unit represented by the following formula (13) is preferred.

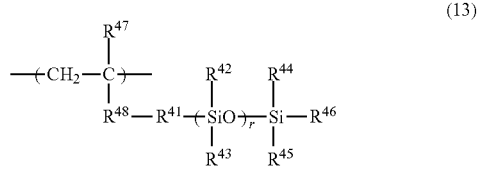

(13)

in which in formula (13), $R^{47}$ represents a hydrogen atom or a methyl group;

$R^{48}$ represents —O—, *—(C=O)—O—, *—(C=O)—NR$^{50}$, *—NR$^{50}$—(C=O)— (in which $R^{50}$ represents a hydrogen atom or an organic group having 1 to 10 carbon atoms; and the symbol * represents the position at which the moiety is bonded to the carbon atom to which $R^{47}$ in formula (13) is bonded), or a phenylene group; and other variables have the same meanings as those of formula (12).

Here, the respective variables in formulae (12) and (13) will be explained.

$R^{41}$ represents a divalent organic group having 1 to 10 carbon atoms. The number of carbon atoms of such a divalent organic group is preferably 2 to 8, more preferably 2 to 6, and even more preferably 2 to 4.

Examples of the divalent organic group include a divalent hydrocarbon group. The divalent hydrocarbon group is preferably a divalent aliphatic hydrocarbon group, and may be linear or branched; and the divalent hydrocarbon group is more preferably an alkylene group. Specific suitable examples of such an alkylene group include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group.

Furthermore, $R^{42}$ and $R^{43}$ independently represent an organic group having 1 to 10 carbon atoms. Note that when there are plural $R^{42}$'s and plural $R^{43}$'s, each of $R^{42}$ may be identical or different, and each of $R^{43}$ may also be identical or different.

Furthermore, the number of carbon atoms of the organic group is preferably 1 to 6, more preferably 1 to 4, and even more preferably 1 or 2.

Examples of the organic group include a hydrocarbon group. The hydrocarbon group may be linear or branched, and is preferably an alkyl group. Specific examples of such an alkyl group include a methyl group, an ethyl group, an n-propyl group, an isopropyl group, an n-butyl group, an isobutyl group, a sec-butyl group, and a tert-butyl group.

$R^{44}$, $R^{45}$ and $R^{46}$ independently represent —OSi($R^{49}$)$_3$ or an organic group having 1 to 10 carbon atoms, and $R^{49}$ independently represent a hydrogen atom or an organic group having 1 to 8 carbon atoms.

The number of carbon atoms of the organic group represented by $R^{44}$, $R^{45}$ and $R^{46}$ or the organic group represented by $R^{49}$ is preferably 1 to 6, more preferably 1 to 4, and even more preferably 1 or 2. Furthermore, examples of the organic group represented by $R^{44}$, $R^{45}$ and $R^{46}$ or the organic group represented by $R^{49}$ include the same groups as the organic groups represented by $R^{42}$.

Furthermore, among the groups for $R^{44}$, $R^{45}$ and $R^{46}$, from the viewpoints of lipid detergency and impartation of hydrophilicity, —OSi($R^{49}$)$_3$ is preferred. Furthermore, among the groups for $R^{49}$, from the viewpoints of lipid detergency and impartation of hydrophilicity, an organic group having 1 to 8 carbon atoms is preferred.

r represents 0 to 200 as an average value; and from the viewpoints of lipid detergency and impartation of hydrophilicity, r is preferably 0 to 100, more preferably 0 to 50, even more preferably 0 to 25, and particularly preferably 0 to 10.

Note that $R^{48}$ is similar to $R^{38}$, and $R^{50}$ is similar to $R^{40}$.

Examples of the monomer from which such a repeating unit (C-2) is derived include 3-[tris(trimethylsiloxy)silyl] propyl (meth)acrylate, 3-[bis(trimethylsiloxy) (methyl)silyl] propyl (meth)acrylate, and silicone (meth)acrylate (for example, X-22-2475 (manufactured by Shin-Etsu Silicones, Inc.) and FM-0711 (manufactured by JNC Corp.)). The repeating unit (C-2) may be used singly or in combination of two or more thereof.

Furthermore, from the viewpoints of lipid detergency, hydrophilization performance, peeling resistance and a lipid adhesion preventive effect, a total content of the repeating unit (C) is preferably 40% by mass or less, more preferably 0.1% to 40% by mass, even more preferably 0.5% to 35% by mass, still more preferably 0.5% to 30% by mass, even more preferably 0.5% 25% by mass, still more preferably 0.5% to 20% by mass, even more preferably 1% to 20% by mass, still more preferably 1% to 15% by mass, still more preferably 1.5% to 15% by mass, and particularly preferably 1.5% to 10% by mass, in the polymer.

Note that the content of the repeating unit (C) may be measured in the same manner as in the case of the content of the repeating unit (A).

Furthermore, a mass ratio between the repeating unit (A) and the repeating unit (B) included in the polymer used for the present invention, [(A):(B)], is, from the viewpoints of lipid detergency, hydrophilization performance, peeling resistance and a lipid adhesion preventive effect and from the viewpoint of enhancing the water-solubility of the polymer, preferably 20:80 to 95:5, more preferably 30:70 to 95:5, even more preferably 40:60 to 90:10, still more preferably 50:50 to 90:10, and particularly preferably 55:45 to 90:10.

Furthermore, in a case where the polymer used for the present invention has a repeating unit (C), from the viewpoints of lipid detergency, hydrophilization performance, peeling resistance and a lipid adhesion preventive effect, the mass ratio, [((A)+(B)):(C)], is preferably 60:40 to 99:1, more preferably 70:30 to 99:1, even more preferably 75:25 to 99:1, still more preferably 80:20 to 98.5:1.5, and particularly preferably 85:15 to 98.5:1.5.

Furthermore, it is particularly preferable that the mass ratio [(A):(B)] is in the range of the mass ratio [(A):(B)] mentioned above, and the mass ratio [((A)+(B)):(C)] is in the range of the mass ratio [((A)+(B)):(C)] mentioned above.

The polymer used for the present invention may be a copolymer, and may be any of a block copolymer, a random copolymer and an alternating copolymer.

A weight average molecular weight ($M_w$) of the polymer used for the present invention is preferably 10,000 to 10,000,000, more preferably 10,000 to 5,000,000, even more preferably 10,000 to 3,000,000, and particularly preferably 10,000 to 2,000,000. When the weight average molecular weight is adjusted to such a range, peeling resistance and handleability are enhanced together.

Furthermore, a number average molecular weight ($M_n$) of the polymer used for the present invention is preferably 10,000 to 10,000,000, more preferably 10,000 to 5,000,000, even more preferably 10,000 to 3,000,000, still more preferably 10,000 to 2,000,000, and particularly preferably 10,000 to 500,000.

Also, a molecular weight distribution ($M_w/M_n$) is preferably 1 to 10, more preferably 1 to 7, and particularly preferably 1 to 5.

Note that the weight average molecular weight, the number average molecular weight, and the molecular weight distribution may be measured by the method described in the following Examples.

The polymer used for the present invention is preferably a polymer which dissolves in a lower alcohol having about 1 to 4 carbon atoms or in water. Furthermore, in a case where the lens solution of the present invention is used for cleaning and storage of contact lenses, the polymer is particularly preferably a polymer which is dissolved in water (water-soluble polymer). Here, in the present specification, the dissolution means that when the polymer is added and mixed into a solvent (25° C.) so as to obtain a polymer solid content of 0.5% by mass, the mixture visually becomes transparent.

Furthermore, the polymer used for the present invention can be obtained by, for example, mixing the monomers from which the respective repeating units are derived, optionally dissolving the resulting mixture in a solvent such as water, acetonitrile, or ECUAMIDE B-100 (manufactured by Idemitsu Kosan Co., Ltd.), and performing radical polymerization by adding a polymerization initiator thereto.

The polymerization initiator used when the radical polymerization is performed is not particularly limited as long as the polymerization initiator is a conventional radical polymerization initiator; and examples thereof include benzoyl peroxide, lauroyl peroxide, diisopropyl peroxydicarbonate, t-butyl peroxy-2-ethylhexanoate, t-butyl peroxypivalate, t-butyl peroxydiisobutyrate, azobis(isobutyronitrile), azobis (isodimethylvaleronitrile), persulfuric acid salts, and persulfuric acid salt-hydrogensulfite salt systems.

Furthermore, an input amount of the polymerization initiator is preferably 0.001 to 10 parts by mass, and more preferably 0.01 to 5 parts by mass, relative to 100 parts by mass of the monomer components. Furthermore, a polymerization temperature is preferably 20° C. to 100° C., and a polymerization time is preferably 0.5 to 48 hours.

The lens solution of the present invention can be produced according to a conventional method, except that a polymer obtainable as described above is used.

As will be disclosed in the following Examples, the lens solution of the present invention has excellent lipid detergency, exhibits high hydrophilization performance, and exhibits an excellent lipid adhesion preventive effect and an excellent lubricity-imparting effect when the lens solution is used to coat a lens. Also, the lens solution exhibits high adsorptiveness to lens surfaces, and unlikely peels.

Therefore, the lens solution of the present invention is useful as a solution for an ophthalmic lens.

The ophthalmic lens is a concept including contact lenses such as a soft contact lens and a hard contact lens, as well as spectacles and an intraocular lens, and the contact lenses may be any of non-hydrous, less hydrous and highly hydrous contact lenses.

Since the lens solution of the present invention has excellent lipid detergency and high hydrophilization performance, the lens solution is especially suitable to be used for cleaning and storage of contact lenses. Also, since the lens solution has high hydrophilization performance, lubricity-imparting performance and peeling resistance, the lens solution is also suitable to be used for coating a contact lens. Furthermore, through a surface treatment method of bringing the lens solution of the present invention into contact with at least a part of a contact lens surface, the surface is hydrophilically modified, so that a contact lens to which lipids are unlikely adsorbed, and lubricity is imparted, and which has excellent sustainability of those effects, can be obtained.

Next, specific embodiments of a solution for contact lens cleaning or storage and a solution for contact lens coating will be explained.

[Contact Lens Cleaning Solution and Contact Lens Storage Solution]

In a case where the lens solution of the present invention is used as a solution for contact lens cleaning or storage, from the viewpoints of lipid detergency, hydrophilization performance and cost, a concentration of the polymer is preferably 0.001% to 10% by mass, more preferably 0.001% to 5% by mass, and even more preferably 0.05% to 3% by mass.

The solution for contact lens cleaning or storage of the present invention may also include, in addition to the polymer described above, a solvent, a surfactant other than the polymer, an isotonic agent, a chelating agent, a pH adjusting agent, a buffering agent, a thickening agent, a stabilizer, a proteolytic enzyme, a pharmacologically active component, a physiologically active component, and the various additives described in Encyclopedia of Pharmaceutical Excipients 2007 (edited by the International Pharmaceutical Excipients Council Japan). Furthermore, one kind among these may be used singly, or two or more thereof may be used in combination.

Examples of the solvent include water; various buffer solutions such as a phosphate buffer solution, a glycine buffer solution, Good's buffer solution, a Tris buffer solution, and an ammonia buffer solution; and an alcohol-based solvent such as methanol, ethanol, and isopropyl alcohol.

Examples of the surfactant include an amphoteric surfactant such as alkyldiaminoethylglycine or a salt thereof (for example, hydrogen chloride salt); a cationic surfactant such as benzalkonium chloride and benzethonium chloride; and an anionic surfactant such as an alkyl benzenesulfonate, an alkyl sulfate, a polyoxyethylene alkyl sulfate, an aliphatic α-sulfomethyl ester, and an α-olefin sulfonate.

Furthermore, examples of the isotonic agent include disodium hydrogen phosphate, sodium dihydrogen phosphate, potassium dihydrogen phosphate, sodium hydrogen sulfite, sodium sulfite, potassium chloride, calcium chloride, sodium chloride, magnesium chloride, potassium acetate, sodium acetate, sodium hydrogen carbonate, sodium carbonate, sodium thiosulfate, magnesium sulfate, glycerin, and propylene glycol.

Examples of the chelating agent include ethylenediaminetetraacetic acid (EDTA), salts of ethylenediaminetetraacetic acid such as disodium ethylenediaminetetraacetate (EDTA.2Na) and trisodium ethylenediaminetetraacetate (EDTA.3Na), citric acid, gluconic acid, tartaric acid, and salts thereof (for example, sodium salts).

Furthermore, examples of the pH adjusting agent include hydrochloric acid, boric acid, ε-aminocaproic acid, citric acid, acetic acid, sodium hydroxide, potassium hydroxide, calcium hydroxide, magnesium hydroxide, sodium hydrogen carbonate, sodium carbonate, borax, triethanolamine, monoethanolamine, diisopropanolamine, sulfuric acid, phosphoric acid, polyphosphoric acid, propionic acid, oxalic acid, gluconic acid, fumaric acid, lactic acid, tartaric acid, malic acid, succinic acid, gluconolactone, and ammonium acetate.

The pH adjusting agent may be used such that the pH value is adjusted to be about 4.0 to 9.0, preferably about 6.0 to 8.0, and more preferably near 7.0.

Examples of the buffering agent include an acid such as citric acid, malic acid, lactic acid, ascorbic acid, maleic acid, gluconic acid, phosphoric acid, boric acid, oxycarboxylic acid, an amino acid such as glycine and glutamic acid, and tris(hydroxymethyl)aminomethane (Tris), or salts thereof (for example, sodium salts); Good Buffer containing taurine or derivatives thereof; and hydroxyalkylamine such as bis (2-hydroxyethyl)iminotris(hydroxymethyl)methane (Bis-Tris).

Furthermore, examples of the thickening agent and the stabilizer include a synthetic organic polymer compound such as polyvinyl alcohol, poly-N-vinylpyrrolidone, polyethylene glycol, polypropylene glycol, and polyacrylamide; a cellulose derivative such as hydroxyethyl cellulose, hydroxypropyl cellulose, and hydroxypropyl methyl cellulose; a starch derivative such as sodium carboxymethyl starch and hydroxyethyl starch; chondroitin sulfate, and a hyaluronic acid salt.

Furthermore, examples of the proteolytic enzyme include biologically derived proteases such as papain, bromelain, glazyme, ficin, trypsin, chymotrypsin, and pancreatin.

Furthermore, examples of the pharmacologically active component and the physiologically active component include the active ingredients in the ophthalmic medicines described in Approval Standards for Manufacturing (Import) of Non-Prescription Drugs, Edition of 2000 (reviewed by Pharmaceutical Affairs Study Group). Specific examples thereof include an antihistamine such as iproheptine, diphenhydramine hydrochloride, chlorpheniramine maleate, ketotifen fumarate, and pemirolast potassium; decongestants such as tetrahydrozoline hydrochloride, naphazoline hydrochloride, naphazoline sulfate, epinephrine hydrochloride, ephedrine hydrochloride, and methylephedrine hydrochloride; disinfectants such as cetylpyridinium, benzalkonium chloride, benzethonium chloride, chlorhexidine hydrochloride, and chlorhexidine gluconate; vitamins such as flavin adenine dinucleotide sodium, cyanocobalamin, retinol acetate, retinol palmitate, pyridoxine hydrochloride, panthenol, calcium pantothenate, and tocopherol acetate; amino acids such as potassium aspartate and magnesium aspartate; and anti-inflammatory agents such as dipotassium glycyrrhizate, pranoprofen, allantoin, azulene, sodium azulene sulfonate, guaiazulene, ε-aminocaproic acid, berberine chloride, berberine sulfate, lysozyme chloride, and licorice; as well as sodium cromoglycate, sodium chondroitin sulfate, sodium hyaluronate, sulfamethoxazole, and sulfamethoxole sodium.

The solution for contact lens cleaning or storage is appropriate for the cleaning or storage of soft contact lenses, and is especially suitable for the cleaning or storage of silicone hydrogel contact lenses.

[Contact Lens Coating Solution]

In a case where the lens solution of the present invention is used as a contact lens coating solution, the concentration of the polymer is preferably 0.001% to 20% by mass, more preferably 0.01% to 15% by mass, and even more preferably 0.1% to 10% by mass, from the viewpoints of hydrophilization performance, lubricity-imparting performance, peeling resistance, and cost.

The contact lens coating agent of the present invention may include, for example, a solvent, a disinfectant, and an antiseptic, in addition to the polymer described above. Examples of the solvent include the same solvents as those used in the solution for contact lens cleaning or storage. The total content of the solvent is preferably 50% to 99.9% by mass, and more preferably 80% to 99.9% by mass.

Furthermore, the contact lens coating solution is appropriate for the coating of soft contact lenses, and is especially suitable for the coating of silicone hydrogel contact lenses.

[Contact Lens]

The contact lens of the present invention has the aforementioned polymer used for the present invention on at least a part of the surface. Specifically, at least a part of the contact lens is coated with the polymer used for the present invention. Furthermore, the surface of the contact lens has been hydrophilically modified as a hydrophilic layer is formed on the contact lens surface.

The contact lens is preferably a soft contact lens, and more preferably a silicone hydrogel contact lens. Furthermore, the contact lens may have been subjected to, for example, a plasma treatment, a UV-ozone treatment, or an internal wetting agent treatment.

[Method for Producing Contact Lens and Method for Surface-Treating Contact Lens]

The method for producing a surface-modified contact lens of the present invention is characterized by including a step of bringing the solution described above into contact with at least a part (preferably, a concave surface) of a contact lens surface. Furthermore, the method for surface-treating a contact lens of the present invention is characterized by including a step of bringing the solution described above into contact with at least a part (preferably, a concave surface) of a contact lens surface.

The contact step in the method for producing a contact lens of the present invention and the method for surface-treating a contact lens of the present invention may be carried out in the same manner as a conventional coating method for a contact lens, except that the lens solution of the present invention is used. Furthermore, the steps other than the contacting step in the method for producing a contact lens of the present invention may be carried out in the same manner as in a conventional production method for a contact lens.

Examples of the coating method include: (1) a method of bringing the lens solution of the present invention into contact with a contact lens, and physically adsorbing the polymer to the resin surface in a solution with the solvent remaining therein; and (2) a method of bringing the lens solution of the present invention into contact with a contact lens, subsequently volatilizing the solvent by drying, and forming a dried film of the polymer on the contact lens surface. Note that in the method (1), after inducing the physical adsorption, a contact lens having the polymer adsorbed thereto can be obtained via a process of removing the remaining solution, usually by a method of, for example, tilting the contact lens so that the solution flows out, lifting up the contact lens from the solution, blowing away the solution on the contact lens, or pouring in a solvent in a large amount.

EXAMPLES

Hereinafter, the present invention will be described in detail by way of Examples, but the present invention is not intended to be limited to these Examples.

Each of analysis conditions in the Examples are as follows.

<Measurement of Molecular Weight>

The weight average molecular weight (Mw) and the number average molecular weight (Mn) were measured by gel permeation chromatography (GPC) based on polystyrene standards, using a TSKgel α-M column manufactured by Tosoh Corp., under the conditions of flow rate: 0.5 ml/min, elution solvent: NMP solvent ($H_3PO_4$: 0.016 M, LiBr: 0.030 M), and column temperature: 40° C.

<NMR Spectrum>

The $^1$H-NMR spectrum was measured using Model AVANCE 500 (500 MHz) manufactured by Bruker Corp., using $d_6$-DMSO as a solvent and an internal reference substance.

Synthesis Example 1

Synthesis of Copolymer (N-1)

1.95 g of methoxypolyethylene glycol (9) monomethacrylate (M-90G (manufactured by Shin Nakamura Chemical Co., Ltd.; hereinafter, referred to as MPEGM), 0.9 g of lauroxypolyethylene glycol (30) monomethacrylate (PLE-1300 (manufactured by NOF Corp.); hereinafter, referred to as LPEGM), 0.03 g of 2,2'-azobis(isobutyronitrile) as a polymerization initiator, and 12 g of ECUAMIDE B-100 (manufactured by Idemitsu Kosan Co., Ltd.) as a solvent were mixed, and the resulting mixture was introduced into a flask. Nitrogen was blown into this flask, the temperature was increased up to 70° C., and polymerization was performed for 8 hours. Thereafter, the resultant was cooled to room temperature. The solution thus obtained was dialyzed with pure water, and thereby an aqueous solution of a copolymer (N-1) was obtained.

In regard to the copolymer (N-1) thus obtained, the content of a repeating unit derived from MPEGM was 65% by mass, and the content of a repeating unit derived from LPEGM was 35% by mass. Note that these contents were measured by $^1$H-NMR.

Furthermore, the weight average molecular weight of the copolymer (N-1) thus obtained was 111,000, the number average molecular weight was 23,300, and the molecular weight distribution was 4.8.

Synthesis Example 2

Synthesis of Copolymer (N-2)

2.10 g of MPEGM, 0.75 g of LPEGM, 0.15 g of 2-ethylhexyl acrylate (manufactured by Tokyo Chemical Industry Co., Ltd.), 0.03 g of 2,2'-azobis(isobutyronitrile) as a polymerization initiator, and 12 g of ECUAMIDE B-100 (manufactured by Idemitsu Kosan Co., Ltd.) as a solvent were mixed, and the resulting mixture was introduced into a flask. Nitrogen was blown into this flask, the temperature was increased up to 70° C., and polymerization was performed for 8 hours. Thereafter, the resultant was cooled to room temperature. The solution thus obtained was dialyzed with pure water, and thereby an aqueous solution of a copolymer (N-2) was obtained.

In regard to the copolymer (N-2) thus obtained, the content of a repeating unit derived from MPEGM was 70% by mass, the content of a repeating unit derived from LPEGM was 25% by mass, and the content of a repeating unit derived from 2-ethylhexyl acrylate was 5% by mass. Note that these contents were measured by $^1$H-NMR.

Furthermore, the weight average molecular weight of the copolymer (N-2) thus obtained was 118,000, the number average molecular weight was 33,800, and the molecular weight distribution was 3.5.

Synthesis Example 3

Synthesis of Copolymer (N-3)

2.10 g of MPEGM, 0.86 g of LPEGM, 0.05 g of a silicone methacrylate represented by the following formula (X) (manufactured by Tokyo Chemical Industry Co., Ltd.), 0.03 g of 2,2'-azobis(isobutyronitrile) as a polymerization initiator, and 12 g of ECUAMIDE B-100 (manufactured by Idemitsu Kosan Co., Ltd.) as a solvent were mixed, and the resulting mixture was introduced into a flask. Nitrogen was blown into this flask, the temperature was increased up to 70° C., and polymerization was performed for 8 hours. Thereafter, the resultant was cooled to room temperature. The solution thus obtained was dialyzed with pure water, and thereby an aqueous solution of a copolymer (N-3) was obtained.

In regard to the copolymer (N-3) thus obtained, the content of a repeating unit derived from MPEGM was 70% by mass, the content of a repeating unit derived from LPEGM was 28.5% by mass, and the content of a repeating unit derived from silicone methacrylate (X) was 1.5% by mass. Note that these contents were measured by $^1$H-NMR.

Furthermore, the weight average molecular weight of the copolymer (N-3) thus obtained was 133,000, the number average molecular weight was 39,400, and the molecular weight distribution was 3.4.

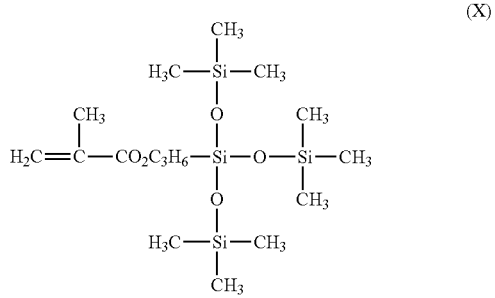

(X)

Synthesis Example 4

Synthesis of Copolymer (N-4)

4.25 g of dimethylacrylamide ((manufactured by Kohjin Co., Ltd.) hereinafter, referred to as DMAA), 0.125 g of N-methacryloyloxyethyl-N,N-dimethylammonium-α-N-methylcarboxybetaine (GLBT (manufactured by Osaka Organic Chemical Industry, Ltd.); hereinafter, referred to as GLBT), 0.50 g of LPEGM, 0.125 g of N-dodecylacrylamide ((manufactured by Tokyo Chemical Industry Co., Ltd.) hereinafter, referred to as DDAA), 0.05 g of 2,2'-azobis(isobutyronitrile) as a polymerization initiator, 31.05 g of acetonitrile (manufactured by Mitsubishi Rayon Co., Ltd.) as a solvent, and 13.50 g of pure water were mixed, and the resulting mixture was introduced into a flask. Nitrogen was blown into this flask, the temperature was increased up to 60° C., and polymerization was performed for 6 hours. Thereafter, the resultant was cooled to room temperature. The solution thus obtained was dialyzed with pure water, and thereby an aqueous solution of a copolymer (N-4) was obtained.

In regard to the copolymer (N-4) thus obtained, the content of a repeating unit derived from DMAA was 85% by mass, the content of a repeating unit derived from GLBT was 2.5% by mass, the content of a repeating unit derived from LPEGM was 10% by mass, and the content of a repeating unit derived from DDAA was 2.5% by mass. Note that these contents were measured by $^1$H-NMR.

Furthermore, the weight average molecular weight of the copolymer (N-4) thus obtained was 515,000, the number average molecular weight was 128,000, and the molecular weight distribution was 4.2.

Synthesis Example 5

Synthesis of Copolymer (N-5)

7.5 g of N-(2-hydroxyethyl)acrylamide ((manufactured by Kohjin Co., Ltd.) hereinafter, referred to as HEAA), 2.00 g of LPEGM, 0.50 g of DDAA, 0.10 g of 2,2'-azobis(isobutyronitrile) as a polymerization initiator, and 39.10 g of isopropanol (manufactured by Tokuyama Corp.) as a solvent were mixed, and the resulting mixture was introduced into a flask. Nitrogen was blown into this flask, the temperature was increased up to 60° C., and polymerization was performed for 6 hours. Thereafter, the resultant was cooled to room temperature. The solution thus obtained was dialyzed with pure water, and thereby an aqueous solution of a copolymer (N-5) was obtained.

In regard to the copolymer (N-5) thus obtained, the content of a repeating unit derived from HEAA was 75% by mass, the content of a repeating unit derived from LPEGM was 20% by mass, and the content of a repeating unit derived from DDAA was 5% by mass. Note that these contents were measured by $^1$H-NMR.

Furthermore, the weight average molecular weight of the copolymer (N-5) thus obtained was 32,000, the number average molecular weight was 16,000, and the molecular weight distribution was 2.0.

Synthesis Example 6

Synthesis of Copolymer (N-6)

4.00 g of DMAA, 0.125 g of acrylic acid ((manufactured by Toagosei Co., Ltd.) hereinafter, referred to as AA), 0.75 g of LPEGM, 0.125 g of DDAA, 0.05 g of 2,2'-azobis(isobutyronitrile) as a polymerization initiator, 31.05 g of acetonitrile (manufactured by Mitsubishi Rayon Co., Ltd.) as a solvent, and 13.50 g of pure water were mixed, and the resulting mixture was introduced into a flask. Nitrogen was blown into this flask, the temperature was increased up to 60° C., and polymerization was performed for 6 hours. Thereafter, the resultant was cooled to room temperature. 0.153 g of sodium hydrogen carbonate was added to the solution thus obtained, and then the mixture was dialyzed with pure water. Thereby, an aqueous solution of a copolymer (N-6) was obtained.

In regard to the copolymer (N-6) thus obtained, the content of a repeating unit derived from DMAA was 80% by mass, the content of a repeating unit derived from AA was 2.5% by mass, the content of a repeating unit derived from LPEGM was 15% by mass, and the content of a repeating unit derived from DDAA was 2.5% by mass. Note that these contents were measured by $^1$H-NMR.

Furthermore, the weight average molecular weight of the copolymer (N-6) thus obtained was 430,000, the number average molecular weight was 108,000, and the molecular weight distribution was 4.0.

Reference Example 1

Synthesis of Copolymer (N-7)

2.85 g of MPEGM, 0.15 g of 2-ethylhexyl acrylate (manufactured by Tokyo Chemical Industry Co., Ltd.), 0.03 g of 2,2'-azobis(isobutyronitrile) as a polymerization initiator, and 12 g of ECUAMIDE B-100 (manufactured by Idemitsu Kosan Co., Ltd.) as a solvent were mixed, and the resulting mixture was introduced into a flask. Nitrogen was blown into this flask, the temperature was increased up to 70° C., and polymerization was performed for 8 hours. Thereafter, the resultant was cooled to room temperature. The solution thus obtained was dialyzed with pure water, and thereby an aqueous solution of a copolymer (N-7) was obtained.

In regard to the copolymer (N-7) thus obtained, the content of a repeating unit derived from MPEGM was 95% by mass, and the content of a repeating unit derived from 2-ethylhexyl acrylate was 5% by mass. Note that these contents were measured by $^1$H-NMR.

Furthermore, the weight average molecular weight of the copolymer (N-7) thus obtained was 115,000, the number average molecular weight was 26,800, and the molecular weight distribution was 4.3.

Reference Example 2

Synthesis of Copolymer (N-8)

2.40 g of DMAA, 0.60 g of 2-ethylhexyl acrylate (manufactured by Tokyo Chemical Industry Co., Ltd.), 0.03 g of 2,2'-azobis(isobutyronitrile) as a polymerization initiator, and 12 g of ECUAMIDE B-100 (manufactured by Idemitsu Kosan Co., Ltd.) as a solvent were mixed, and the resulting mixture was introduced into a flask. Nitrogen was blown into this flask, the temperature was increased up to 70° C., and polymerization was performed for 8 hours. Thereafter, the resultant was cooled to room temperature. The solution thus obtained was dialyzed with pure water, and thereby an aqueous solution of a copolymer (N-8) was obtained.

In regard to the copolymer (N-8) thus obtained, the content of a repeating unit derived from DMAA was 80% by mass, and the content of a repeating unit derived from 2-ethylhexyl acrylate was 20% by mass. Note that these contents were measured by $^1$H-NMR.

Furthermore, the weight average molecular weight of the copolymer (N-8) thus obtained was 49,000, the number average molecular weight was 14,300, and the molecular weight distribution was 3.4.

Each of the copolymers (N-1) to (N-8) obtained in the various Synthesis Examples and Reference Examples was mixed with purified water at 25° C., and the concentration was adjusted to 0.5% by mass. The various copolymers were all dissolved in purified water.

Example 1

A treatment agent was obtained by mixing 0.5 parts by mass of the copolymer (N-1) obtained in Synthesis Example 1, with 99.5 parts by mass of a phosphate buffered physiological saline (hereinafter, referred to as PBS).

Examples 2 to 6

Treatment agents were obtained in the same manner as in Example 1, by mixing 0.5 parts by mass of each of the copolymers (N-2) to (N-6) obtained in Synthesis Examples 2 and 3, with 99.5 parts by mass of PBS.

Comparative Examples 1 and 2

Treatment agents were obtained in the same manner as in Example 1, by mixing 0.5 parts by mass of each of the copolymers (N-7) and (N-8) obtained in Reference Examples 1 and 2, with 99.5 parts by mass of PBS.

Comparative Example 3

A treatment agent was obtained by mixing 0.5 parts by mass of POLOXAMER 407 (manufactured by Sigma-Aldrich Co.), which is a nonionic surfactant used in a general contact lens detergent, with 99.5 parts by mass of PBS.

Test Example 1

Lipid Cleaning Test

First, prior to the test, 99% by mass of lipid triglycerides and 1% by mass of Sudan Black B (dye) were thermally fused, and a lipid solution was prepared. 200 µL of the lipid solution was dropped into a screw cap bottle such that the liquid surface was maintained flat, and then the lipid solution was cooled to room temperature. Thus, a screw cap bottle containing colored pseudo-eye discharge pellets was prepared.

Subsequently, 1 mL of each of the treatments of Examples and Comparative Examples was introduced into this screw cap bottle containing pellets, and the bottle was shaken for 14 hours at room temperature. Thereby, the colored pseudo-eye discharge pellets were dissolved. After completion of shaking, each of the treatment agents was removed from the screw cap bottle, and the absorbance at 570 nm of each agent was measured using Model 680 Microplate Reader (manufactured by BIO-RAD Laboratories, Inc).

Furthermore, the same procedure as described above was carried out, except that PBS was used instead of the treatments, and the absorbance at 570 nm was measured. This was used as a control, and the difference of absorbance was calculated by the following expression. The test results are presented in Table 2.

(Difference of absorbance)=(Absorbance of each treatment agent)−(absorbance of control)

Note that a higher difference of absorbance implies that the dissolving power for the colored pseudo-eye discharge pellets is higher, that is, the lipid detergency is superior.

Test Example 2

Hydrophilization Performance Test

First, as contact lenses, commercially available contact lenses (manufactured by Johnson & Johnson, Inc., ACUVUE OASYS) formed from a silicone hydrogel were prepared, and these contact lenses were washed 3 times with PBS.

Subsequently, the contact lenses were respectively immersed in 1 mL of each of the treatment agents of Examples and Comparative Examples, and the contact lenses were left to stand for 2 hours at room temperature and then were washed 3 times with PBS. After the moisture on the contact lens surfaces was wiped out, the contact angle in accordance with a water drop method was measured using a contact angle meter DM-701 (manufactured by Kyowa Interface Science Co., Ltd).

The test results as the contact angle immediately after coating are presented in Table 2. Note that the control in the table represents the results obtained by a test carried out as described above using PBS instead of the various treatment agents.

Test Example 3

Coating Durability Test

The contact lenses treated with the various treatment agents used for the measurement in Test Example 2 were washed 10 times by rubbing using a commercially available contact lens cleaning solution (OPTI-FREE PLUS (manufactured by Alcon, Inc.)), and the lenses were rinsed and then were washed 3 times with PBS. Subsequently, after the moisture on the contact lens surfaces was wiped out, the contact angles in accordance with a water drop method were measured using a contact angle meter (DM-701 (manufactured by Kyowa Interface Science Co., Ltd.)).

The test results as the contact angle after washing with rubbing are presented in Table 2. The control in the table represents the results obtained by a test carried out as described above using PBS instead of the various treatment agents.

Test Example 4

Lipid Antifouling Test

First, prior to the test, a lipid solution was obtained by homogenizing oleic acid: 1.20% by mass, linolic acid: 1.20% by mass, tripalmitic acid: 16.23% by mass, cetyl alcohol: 4.01% by mass, palmitic acid: 1.20% by mass, cetyl palmitate: 16.23% by mass, cholesterol: 1.60% by mass, cholesterol palmitate: 1.60% by mass, and lecithin: 56.71% by mass by heating and stirring. 0.5 parts by mass of this lipid solution and 99.5 parts by mass of water were mixed and emulsified, and thus an artificial lipid solution was prepared.

Subsequently, as contact lenses, commercially available contact lenses (manufactured by Johnson & Johnson, Inc., ACUVUE OASYS) formed from a silicone hydrogel were prepared, and these contact lenses were washed 3 times with PBS. Subsequently, each of the contact lenses were respectively immersed in 1 mL of each of the treatment agents of Examples and Comparative Examples, and the contact lenses were left to stand for 2 hours at room temperature and then were washed 3 times with PBS.

Subsequently, each of the contact lenses thus treated were immersed in 1 mL of the artificial lipid solution, and the contact lenses were shaken for 1 hour. Subsequently, the contact lenses were removed, and were washed 3 times with PBS and then dried under reduced pressure. Thereafter, each of these contact lenses was immersed in 1 mL of an ethanol/diethyl ether (75/25 vol %) solution, and was left to stand for 30 minutes. Thereby, the lipids remaining on the lenses were extracted. 0.5 mL of this extract solution was collected in a test tube, and the solvent was evaporated at 90° C.

Subsequently, 0.5 mL of concentrated sulfuric acid was added to the test, and the mixture was heated for 30 minutes at 90° C. This solution was cooled to room temperature, and then 2.5 mL of a 0.6 mass % vanillin aqueous solution/phosphoric acid (20/80 vol %) solution was added thereto. The mixture was maintained for 15 minutes at 37° C. This solution was cooled to room temperature, and then the absorbance at 540 nm was measured. Solutions of known lipid concentrations were previously analyzed by the same method as described above, and thereby a calibration curve was prepared. Thus, the amounts of lipids adsorbed to the contact lenses were determined from the absorbances of the analysis results.

The test results are presented as the lipid antifouling amounts in Table 2. Note that the control in the table represents the results obtained by a test carried out as described above using PBS instead of the various treatment agents. Furthermore, the lipid antifouling amount represents the amount of lipid adhesion that is decreased compared to the control, and as the value is larger, the lipid antifouling effect is superior.

Test Example 5

Lubricity Test

First, a silicone hydrogel was prepared prior to the test. That is, 50 parts by mass of the silicone methacrylate represented by formula (X) (manufactured by Tokyo Chemical Industry Co., Ltd.), 45 parts by mass of DMAA (manufactured by Kohjin Co., Ltd.), 5 parts by mass of polyethylene glycol dimethacrylate n t 4 (manufactured by Tokyo Chemical Industry Co., Ltd.), and 1 part by mass of 2,2-dimethoxy-2-phenylacetophenone were mixed, and the resulting mixture was poured into a glass Petri dish. The mixture was irradiated with UV in air such that the amount of UV irradiation was 1.5 J/cm$^2$, and thus a transparent polymerization product was obtained. This polymerization product was swollen with ion-exchanged water, and then was stored in PBS. Thus, a silicone hydrogel was obtained.

Subsequently, the silicone hydrogel thus produced was washed 3 times with PBS, and then was immersed in 1 mL of each of the treatments of the Examples and Comparative Examples. The hydrogel was left to stand for 2 hours at room temperature, and then was washed 3 times with PBS.

Subsequently, for the silicone hydrogel after washing, the lubricity perceived when the silicone hydrogel was touched with a dry finger was evaluated by five subjects in accordance with the following criteria based on grades 1 to 4, and the average value of the lubricity grades was calculated.

(Evaluation Criteria for Lubricity)
Grades
1 Equal to base material (control)
2 Having slight lubricity.
3 Having lubricity generally without squeaking
4 Having high lubricity The test results are presented as lubricity in Table 2. Note that the control in the table represents the results obtained by a test carried out as described above using PBS instead of the various treatment agents.

TABLE 1

|  |  | Synthesis Example 1 N-1 | Synthesis Example 2 N-2 | Synthesis Example 3 N-3 | Synthesis Example 4 N-4 | Synthesis Example 5 N-5 | Synthesis Example 6 N-6 | Reference Example 1 N-7 | Reference Example 2 N-8 |
|---|---|---|---|---|---|---|---|---|---|
| (A) | MPEGM | 65 mass % | 70 mass % | 70 mass % | — | — | — | 95 mass % | — |
|  | DMAA | — | — | — | 85 mass % | — | 80 mass % | — | 80 mass % |
|  | HEAA | — | — | — | — | 75 mass % | — | — | — |
|  | GLBT | — | — | — | 2.5 mass % | — | — | — | — |
|  | AA | — | — | — | — | — | 2.5 mass % | — | — |
| (B) | LPEGM | 35 mass % | 25 mass % | 28.5 mass % | 10 mass % | 20 mass % | 15 mass % | — | — |
| (C) | 2-EHA (*1) | — | 5 mass % | — | — | — | — | 5 mass % | 20 mass % |
|  | DDAA | — | — | — | 2.5 mass % | 5 mass % | 2.5 mass % | — | — |
|  | Si-MA (*2) | — | — | 1.5 mass % | — | — | — | — | — |
|  | Water-solubility (0.5 mass %) | Transparent | Transparent | Transparent | Transparent | Transparent | Transparent | Transparent | Transparent |

*1: 2-Ethylhexyl acrylate,
*2: Silicone methacrylate

TABLE 2

|  |  |  | Example | | | | | | Comparative Example | | |
|---|---|---|---|---|---|---|---|---|---|---|---|
|  |  | Control | 1 | 2 | 3 | 4 | 5 | 6 | 1 | 2 | 3 |
|  | Polymer | — | N-1 | N-2 | N-3 | N-4 | N-5 | N-6 | N-7 | N-8 | POLOXAMER 407 |
|  | Difference of absorbance | 0 | +0.048 | +0.07 | +0.064 | +0.040 | +0.055 | +0.042 | +0.036 | +0.028 | +0.05 |
| Contact angle (°) | Immediately after coating | 69 | 35 | 15 | 16 | 12 | 14 | 13 | 60 | 71 | 41 |
|  | After washing by rubbing | 76 | 47 | 41 | 37 | 27 | 43 | 35 | 75 | 84 | 83 |
|  | Lipid antifouling amount (μg) | 0 | 9 | 11 | 7 | 8 | 8 | 9 | 0 | 0 | 0 |
|  | Lubricity | 1 | 2.6 | 2.8 | 3.2 | 3.8 | 3.0 | 3.4 | 1.8 | 2.2 | 2.4 |

As indicated in Table 2, the solutions of Examples 1 to 6 exhibited excellent properties in lipid detergency, hydrophilization performance, peeling resistance, a lipid adhesion preventive effect, and a lubricity-imparting effect. Furthermore, the solutions of Examples 2 to 6 exhibited particularly excellent hydrophilization performance and peeling resistance.

The invention claimed is:

1. A solution comprising a polymer having 2.5% to 95% by mass of the following repeating unit (A) and 2.5% to 95% by mass of the following repeating unit (B):
   (A) a hydrophilic repeating unit; and
   (B) a repeating unit having a polyoxyalkylene group in a side chain and having the end of the side chain formed from an alkyl group having 5 to 30 carbon atoms, an alkanoyl group having 5 to 30 carbon atoms, or an aryl group,
   wherein the repeating unit (A) comprises a repeating unit (A-3) represented by the following formula (4) and a betaine-containing repeating unit (A-6) represented by the following formula (7):

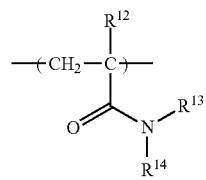

(4)

in which in formula (4),
   $R^{12}$ represents a hydrogen atom or a methyl group; and
   $R^{13}$ and $R^{14}$ each independently represent a hydrogen atom, an alkyl group having 1 to 6 carbon atoms, or a hydroxyalkyl group,

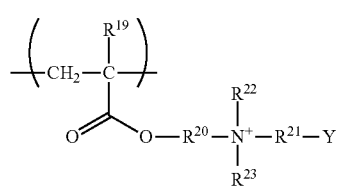

(7)

in which in formula (7),

Y represents —(C=O)O⁻, —(O=S=O)O⁻, —O(O=S=O)O⁻, —(S=O)O⁻, —O(S=O)O⁻, —OP(=O)(OR²⁴)O⁻, —OP(=O)(R²⁴)O⁻, —P(=O)(OR²⁴)O⁻, or —P(=O)(R²⁴)O⁻, wherein $R^{24}$ represents an alkyl group having 1 to 3 carbon atoms;

$R^{19}$ represents a hydrogen atom or a methyl group;

$R^{20}$ and $R^{21}$ each independently represent a divalent organic group having 1 to 10 carbon atoms; and $R^{22}$ and $R^{23}$ each independently represent a hydrocarbon group having 1 to 10 carbon atoms.

2. The solution according to claim 1, wherein the repeating unit (B) is represented by the following formula (10):

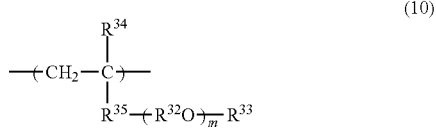
(10)

in which in formula (10), $R^{32}$ represent an alkylene group having 2 to 4 carbon atoms;

$R^{33}$ represents an alkyl group having 5 to 30 carbon atoms, an alkanoyl group having 5 to 30 carbon atoms, or an aryl group;

$R^{34}$ represents a hydrogen atom or a methyl group;

$R^{35}$ represents —O—, —(C=O)—O—, —(C=O)—NR³⁶—, —NR³⁶—(C=O)—, wherein $R^{36}$ represents a hydrogen atom or an organic group having 1 to 10 carbon atoms; and the symbol  represents the position at which the moiety is bonded to the carbon atom to which $R^{34}$ in formula (10) is bonded, or a phenylene group; and m represents 2 to 100 as an average value.

3. The solution according to claim 1, wherein the polymer further comprises 40% by mass or less of a repeating unit (C), the repeating unit (C) being one or more selected from the group consisting of a repeating unit represented by the following formula (11), and a repeating unit having a group represented by the following formula (12) at the end of a side chain:

(11)

in which in formula (11), $R^{37}$ represent a hydrogen atom or a methyl group;

$R^{38}$ represents —O—, *—(C=O)—O—, *—(C=O)—NR⁴⁰—, *—NR⁴⁰—(C=O)—, wherein $R^{40}$ represents a hydrogen atom or an organic group having 1 to 10 carbon atoms; and the symbol * represents the position at which the moiety is bonded to the carbon atom to which $R^{37}$ in formula (11) is bonded, or a phenylene group; and $R^{39}$ represents a hydrocarbon group having 4 to 30 carbon atoms,

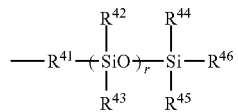
(12)

in which in formula (12), $R^{41}$ represents a divalent organic group having 1 to 10 carbon atoms;

$R^{42}$ and $R^{43}$ each independently represent an organic group having 1 to 10 carbon atoms;

$R^{44}$, $R^{45}$ and $R^{46}$ each independently represent —OSi($R^{49}$)₃, wherein $R^{49}$'s each independently represent a hydrogen atom or an organic group having 1 to 8 carbon atoms, or an organic group having 1 to 10 carbon atoms; and r represents 0 to 200 as an average value.

4. The solution according to claim 1, wherein the polymer is a water-soluble polymer.

5. The solution according to claim 4, formulated for cleaning or storage of a contact lens.

6. The solution according to claim 5, comprising 0.001% to 10% by mass of the polymer.

7. The solution according to claim 1 formulated, for coating a contact lens.

8. A method for producing a surface-modified contact lens, comprising bringing the solution according to claim 1 into contact with at least a part of a contact lens surface.

9. A contact lens comprising, in at least a part of the surface, a polymer containing 2.5% to 95% by mass of the following repeating unit (A) and 2.5% to 95% by mass of the following repeating unit (B):

(A) a hydrophilic repeating unit; and (B) a repeating unit having a polyoxyalkylene group in a side chain and having the end of the side chain formed from an alkyl group having 5 to 30 carbon atoms or an alkanoyl group having 5 to 30 carbon atoms, wherein the repeating unit (A) comprises a repeating unit (A-3) represented by the following formula (4) and a betaine-containing repeating unit (A-6) represented by the following formula (7):

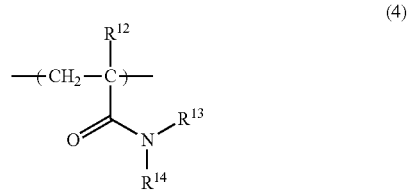
(4)

in which in formula (4), $R^{12}$ represents a hydrogen atom or a methyl group; and $R^{13}$ and $R^{14}$ each independently represent a hydrogen atom, an alkyl group having 1 to 6 carbon atoms, or a hydroxyalkyl group,

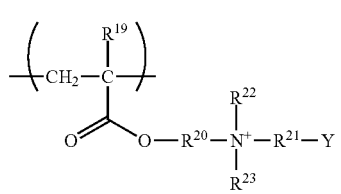

(7)

in which in formula (7),

Y represents —(C=O)O⁻, —(O=S=O)O⁻, —O(O=S=O)O⁻, —(S=O)O⁻, —O(S=O)O⁻, —OP(=O)(OR²⁴)O⁻, —OP(=O)(R²⁴)O⁻, —P(=O)(OR²⁴)O⁻, or —P(=O)(R²⁴)O⁻, wherein $R^{24}$ represents an alkyl group having 1 to 3 carbon atoms;

$R^{19}$ represents a hydrogen atom or a methyl group;

$R^{20}$ and $R^{21}$ each independently represent a divalent organic group having 1 to 10 carbon atoms; and $R^{22}$ and $R^{23}$ each independently represent a hydrocarbon group having 1 to 10 carbon atoms.

10. The solution according to claim 1, wherein a content of the repeating unit (A) is 30 to 95% by mass in the polymer, and a content of the repeating unit B is 2.5% to 70% by mass in the polymer.

11. The solution according to claim 1, wherein a content of the repeating unit (A) is 40 to 95% by mass in the polymer, and a content of the repeating unit B is 2.5 to 60% by mass in the polymer, and wherein the repeating unit (A) is dimethylacrylamide/N-methacryloyloxyethyl-N,N-dimethylammonium-α-N-methyl-carboxybetaine, and the repeating unit (B) is lauroxypolyethylene glycol monomethacrylate.

12. A polymer comprising 2.5% to 95% by mass of the following repeating unit (A) and 2.5% to 95% by mass of the following repeating unit (B):

(A) a hydrophilic repeating unit; and (B) a repeating unit having a polyoxyalkylene group in a side chain and having the end of the side chain formed from an alkyl group having 5 to 30 carbon atoms, an alkanoyl group having 5 to 30 carbon atoms, or an aryl group, wherein the repeating unit (A) comprises a repeating unit (A-3) represented by the following formula (4) and a betaine-containing repeating unit (A-6) represented by the following formula (7):

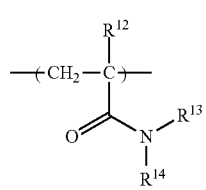

(4)

in which in formula (4), $R^{12}$ represents a hydrogen atom or a methyl group; and $R^{13}$ and $R^{14}$ each independently represent a hydrogen atom, an alkyl group having 1 to 6 carbon atoms, or a hydroxyalkyl group,

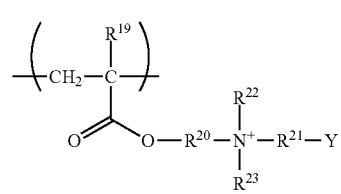

(7)

in which in formula (7),

Y represents —(C=O)O⁻, —(O=S=O)O⁻, —O(O=S=O)O⁻, —(S=O)O⁻, —O(S=O)O⁻, —OP(=O)(OR²⁴)O⁻, —OP(=O)(R²⁴)O⁻, —P(=O)(OR²⁴)O⁻, or —P(=O)(R²⁴)O⁻, wherein $R^{24}$ represents an alkyl group having 1 to 3 carbon atoms;

$R^{19}$ represents a hydrogen atom or a methyl group;

$R^{20}$ and $R^{21}$ each independently represent a divalent organic group having 1 to 10 carbon atoms; and $R^{22}$ and $R^{23}$ each independently represent a hydrocarbon group having 1 to 10 carbon atoms.

13. The polymer according to claim 12, wherein $R^{13}$ and $R^{14}$ in formula (4) each independently represent a hydrogen atom or an alkyl group having 1 to 6 carbon atoms.

14. The polymer according to claim 12, wherein $R^{20}$ and $R^{21}$ in formula (7) each independently represent a divalent hydrocarbon group having 1 to 10 carbon atoms.

15. The polymer according to claim 12, wherein the repeating unit (B) is represented by the following formula (10):

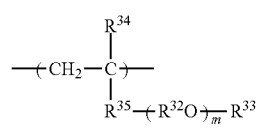

(10)

in which in formula (10), $R^{32}$ represent an alkylene group having 2 to 4 carbon atoms;

$R^{33}$ represents an alkyl group having 5 to 30 carbon atoms, an alkanoyl group having 5 to 30 carbon atoms, or an aryl group;

$R^{34}$ represents a hydrogen atom or a methyl group;

$R^{35}$ represents —O—, —(C=O)—O—, —(C=O)—NR³⁶—, —NR³⁶—(C=O)—, wherein $R^{36}$ represents a hydrogen atom or an organic group having 1 to 10 carbon atoms; and the symbol  represents the position at which the moiety is bonded to the carbon atom to which $R^{34}$ in formula (10) is bonded, or a phenylene group; and m represents 2 to 100 as an average value.

16. The polymer according to claim 15, wherein $R^{33}$ in formula (10) represents an alkyl group having 5 to 30 carbon atoms.

17. The polymer according to claim 15, wherein $R^{35}$ in formula (10) represents —(C=O)—O⁻, —(C=O)—NR³⁶—, **—NR³⁶—(C=O)— or a phenylene group.

18. The polymer according to claim 12, further comprising one or more of a repeating unit (C) selected from the group consisting of a repeating unit (C-1) represented by the following formula (11), and a repeating unit (C-2) having a group represented by the following formula (12) at the end of a side chain:

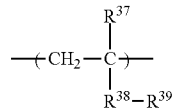
(11)

in which in formula (11),
$R^{37}$ represent a hydrogen atom or a methyl group;
$R^{38}$ represents —O—, *—(C=O)—O—, *—(C=O)—NR$^{40}$—, *—NR$^{40}$—(C=O)—, wherein $R^{40}$ represents a hydrogen atom or an organic group having 1 to 10 carbon atoms; and the symbol * represents the position at which the moiety is bonded to the carbon atom to which $R^{37}$ in formula (11) is bonded), or a phenylene group; and
$R^{39}$ represents a hydrocarbon group having 4 to 30 carbon atoms,

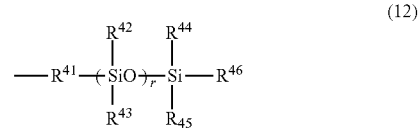
(12)

in which in formula (12),
$R^{41}$ represents a divalent organic group having 1 to 10 carbon atoms;
$R^{42}$ and $R^{43}$ each independently represent an organic group having 1 to 10 carbon atoms;
$R^{44}$, $R^{45}$ and $R^{46}$ each independently represent —OSi$(R^{49})_3$, wherein $R^{49}$'s each independently represent a hydrogen atom or an organic group having 1 to 8 carbon atoms, or an organic group having 1 to 10 carbon atoms; and
r represents 0 to 200 as an average value.

19. The polymer according to claim 18, wherein the repeating unit (C) is the repeating unit (C-1).

20. The polymer according to claim 18, wherein a content of the repeating unit (C) is 0.1% by mass to 40% by mass.

* * * * *